(12) United States Patent
Masri et al.

(10) Patent No.: US 8,609,388 B2
(45) Date of Patent: Dec. 17, 2013

(54) MODIFIED FAMILY 5 CELLULASES AND USES THEREOF

(75) Inventors: Nabil Masri, Gatineau (CA); Patrick St-Pierre, Gatineau (CA); Sandra Mortimer, Orleans (CA); Christopher M. D. Hill, Nepean (CA)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/583,238

(22) PCT Filed: Mar. 11, 2011

(86) PCT No.: PCT/CA2011/000267
§ 371 (c)(1),
(2), (4) Date: Sep. 7, 2012

(87) PCT Pub. No.: WO2011/109905
PCT Pub. Date: Sep. 15, 2011

(65) Prior Publication Data
US 2013/0095554 A1    Apr. 18, 2013

Related U.S. Application Data

(60) Provisional application No. 61/312,864, filed on Mar. 11, 2010.

(51) Int. Cl.
*C12N 9/42* (2006.01)
(52) U.S. Cl.
USPC .................... 435/209; 435/252.3; 435/183
(58) Field of Classification Search
None
See application file for complete search history.

(56) References Cited

U.S. PATENT DOCUMENTS

| 5,700,686 A | 12/1997 | Foody et al. |
| 5,858,767 A | 1/1999 | Miettinen-Oinonen et al. |
| 5,874,293 A | 2/1999 | Miettinen-Oinonen et al. |
| 5,916,799 A | 6/1999 | Foody et al. |
| 6,015,703 A | 1/2000 | White et al. |
| 2003/0054535 A1 | 3/2003 | Himmel et al. |
| 2007/0244020 A1 | 10/2007 | Alapuranen et al. |
| 2008/0076152 A1 | 3/2008 | St-Pierre et al. |

FOREIGN PATENT DOCUMENTS

| EP | 0 866 165 | 8/2003 |
| WO | 19921017574 | 10/1992 |
| WO | 96/23928 A1 | 8/1996 |
| WO | 2008/088724 A2 | 7/2008 |
| WO | 2008/151043 A1 | 12/2008 |
| WO | 20101060188 | 6/2010 |
| WO | 20101076387 | 7/2010 |

OTHER PUBLICATIONS

Baker, et al., "Catalytically Enhanced Endocellulase Cel5A from *Acidothermus cellulolyticus*", Appl. Biochem. Biotechnol., vol. 121-124 (2005) 129-48.
Bhikhabhai, et al., "Isolation of Cellulolytic Enzymes from *Trichoderma reesei* QM 9414", J. Appl. Biochem., vol. 6, (1984) 336-45.
Bortoli-German, et al., "Informational Suppression to Investigate Structural Functional and Evolutionary Aspects of the *Erwinia chrysanthemi* Cellulase Egz", J. Mol. Biol., vol. 246 (1995) 82-94.
Cantarel, et al., "The Carbohydrate-Active EnZymes database (CAZy): an expert resource for Glycogenomics", Nucleic. Acids Res., vol. 37 (2008) D233-38.
Davies, et al., "Structures and mechanisms of glycosyl hydrolases", Structure, vol. 3, No. 9 (1995) 853-59.
Fukuda, et al., "Enhancement of Cellulase Activity by Clones Selected from the Combinatorial Library of the Cellulose-Binding Domain by Cell Surface Engineering", Biotechnol. Prog., vol. 22 (2006) 933-38.
Ghose, Measurement of Cellulase Activities, Pure & Appl. Chem., vol. 59, No. 2 (1987) 257-68.
Ito, "Improvement of Cellulose-Degrading Ability of a Yeast Strain Displaying *Trichoderma reesei* Endoglucanase II by Recombination of Cellulose-Binding Domains", Biotechnol. Frog., vol. 20 (2004) 688-91.
Lin, et al., "Improved catalytic efficiency of Endo-β-1,4-glucanase from *Bacillus subtilis* BME-15 by directed evolution", Appl. Microbiol. Biotechnol., vol. 82 (2008) 671-79.
Ly, et al., "Mutagenesis of Glycosidases", Annu. Rev. Biochem., vol. 68 (1999) 487-522.
Macarron, et al., "Identification of an essential glutamate residue in the active site of endoglucanase III from *Trichoderma reesei*", FEBS Lett. vol. 316, No. 2 (1993) 137-140.
Mahadevan, et al., "Site-directed mutagenesis and CBM engineering of Cel5A (*Thermatoga maritima*)", Fems Microbiol. Lett., vol. 287 (2008) 205-11.
Miettinen-Oinonen, et al., "Enhanced Production of *Trichoderma reesei* Endoglucanases and Use of the New Cellulase Preparations in Producing the Stonewashed Effect on Denim Fabric", Appl. Environ. Microbiol., vol. 68, No. 8 (2002) 3956-64.

(Continued)

*Primary Examiner* — Anand Desai
*Assistant Examiner* — R. P. R.
(74) *Attorney, Agent, or Firm* — Kristin J. McNamara

(57) ABSTRACT

The present invention relates to a modified Family 5 cellulase comprising a substitution of an amino acid at position 363 with a non-native alanine, serine or threonine, the position determined from alignment of the modified Family 5 cellulase with amino acids 71-397 of a *Trichoderma reesei* Cel5A amino acid sequence as set forth in SEQ ID NO:1 and enzyme mixtures comprising same. Additionally provided is a genetic construct comprising a nucleic acid sequence encoding the modified Family 5 cellulase and a genetically modified microbe comprising the genetic construct. The invention also provides a process for producing the modified Family 5 cellulase.

15 Claims, 16 Drawing Sheets

(56) References Cited

OTHER PUBLICATIONS

Nakamura, et al., "Construction and Characterization of the Chimeric Enzymes between the *Bacillus subtilis* Cellulase and an Alkalophilic Bacillus Cellulase", J. Biol. Chem., vol. 266, No. 3 (1991) 1579-83.

Ohnishi, et al., "Transcriptional regulation of two endoglucanase-encoding genes (cel3 and cel4) from the wood-degrading basidiomycete Polyporus arcularius", FEMS Microbio. Letters, vol. 274 (2007) 218-25.

Park, et al., "Identification of two amino acids contributing the high enzyme activity in the alkaline pH range of an alkaline endoglucanase from a *Bacillus* sp." Protein Eng., vol. 6, No. 8 (1993) 921-26.

Qin, et al., "The role of the site 342 in catalytic efficiency and pH optima of endoglucanase II from *Trichoderma reesei* as probed by saturation mutagenesis", Biocatal. Biotransformation., vol. 26, No. 5(2008) 378-82.

Qin, et al., "Engineering endoglucanase II from *Trichoderma reesei* to improve the catalytic efficiency at a higher pH optimum", J. Biotechnol., vol. 135 (2008) 190-95.

Stahlberg, et al., "A binding-site-deficient, catalytically active, core protein of endoglucanase III from the culture filtrate of *Trichoderma reesei*", Eur. J. Biochem., vol. 173 (1988) 179-83.

Wang, et al., "Directed evolution for engineering pH profile of endoglucanase III from *Trichoderma reesei*", Biomol. Eng., vol. 22 (2005) 89-94.

Wang, et al., "Glu280 is the Nucleophile in the Active Site of *Clostridium thermocellum* CelC, a Family a endo-β-1,4- glucanase", J. Biolog. Chem., vol. 268, No. 19 (1993) 14096-102.

Xiao, et al., "Cold adaptation of a mesophilic cellulase, EG III from *Trichoderma reesei*, by directed evolution", Science in China, vol. 45, No. 4 (2002) 337-43.

Zhang, et al., "Determination of the number-average degree of polymerization of cellodextrins and cellulose with application to enzymatic hydrolysis", Biomacromolecules, vol. 6, No. 3 (2005) 1510-515.

Nakazawa et al., Applied Microbiol Biotech, pp. 681-689 (2008).

Ng et al., Extremophiles, pp. 425-435 (2009).

Pere et al., Biotechnology, pp. 247-255 (2001).

Qin., Protein Expression Purification, pp. 1-6 (2007).

Eijsink et al., Biomolecular Engineering, vol. 22, pp. 21-30 (2005).

```
SEQUENCE LISTING

<160> NUMBER OF SEQ ID NOS: 28

<210> SEQ ID NO 1
<211> LENGTH: 397
<212> TYPE: PRT
<213> ORGANISM: Trichoderma reesei

<400> SEQUENCE: 1

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile Pro Gly Ala Thr Thr Ile Thr Thr Ser Thr Arg Pro
        35                  40                  45

Pro Ser Gly Pro Thr Thr Thr Thr Arg Ala Thr Ser Thr Ser Ser Ser
    50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

Val Tyr Pro Pro Leu Lys Asn Phe Thr Gly Ser Asn Asn Tyr Pro Asp
            100                 105                 110

Gly Ile Gly Gln Met Gln His Phe Val Asn Asp Asp Gly Met Thr Ile
        115                 120                 125

Phe Arg Leu Pro Val Gly Trp Gln Tyr Leu Val Asn Asn Asn Leu Gly
    130                 135                 140
```

```
Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Ile Ile Gly Gln Gly Gly Pro Thr Asn Ala
            180                 185                 190

Gln Phe Thr Ser Leu Trp Ser Gln Leu Ala Ser Lys Tyr Ala Ser Gln
                195                 200                 205

Ser Arg Val Trp Phe Gly Ile Met Asn Glu Pro His Asp Val Asn Ile
            210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Leu Ser Gln
                260                 265                 270

Val Thr Asn Pro Asp Gly Ser Thr Thr Asn Leu Ile Phe Asp Val His
            275                 280                 285

Lys Tyr Leu Asp Ser Asp Asn Ser Gly Thr His Ala Glu Cys Thr Thr
            290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
                340                 345                 350

Ser Asp Val Tyr Leu Gly Tyr Val Gly Trp Gly Ala Gly Ser Phe Asp
                355                 360                 365

Ser Thr Tyr Val Leu Thr Glu Thr Pro Thr Gly Ser Gly Asn Ser Trp
            370                 375                 380

Thr Asp Thr Ser Leu Val Ser Ser Cys Leu Ala Arg Lys
385                 390                 395

<210> SEQ ID NO 2
<211> LENGTH: 320
<212> TYPE: PRT
<213> ORGANISM: Penicillium janthinellum

<400> SEQUENCE: 2

Thr Gly Lys Val Arg Phe Ala Gly Val Asn Ile Ala Gly Phe Asp Phe
1               5                   10                  15

Gly Val Val Thr Ser Gly Thr Gln Asp Leu Ser Gln Val Val Asp Glu
                20                  25                  30

Ser Val Asp Gly Val Asn Gln Met Ser His Phe Val Asn Ala Asp Thr
            35                  40                  45

Phe Asn Ile Phe Arg Leu Pro Thr Gly Trp Gln Phe Ile Val Asn Asn
        50                  55                  60

Asn Leu Gly Gly Ser Leu Asp Ser Asn Asn Phe Gly Lys Tyr Glu Gln
65                  70                  75                  80

Val Gly Ser Gly Leu Ser Leu Ser Gly Ala Tyr Cys Ile Val Asp Ile
                85                  90                  95

His Asn Tyr Ala Arg Trp Asn Gly Val Ile Gly Gln Gly Gly Pro
            100                 105                 110

Thr Asp Asp Gln Phe Ile Ser Leu Trp Thr Gln Leu Ala Thr His Tyr
            115                 120                 125
```

```
Lys Ser Asn Ser Arg Val Ile Phe Gly Ile Met Asn Glu Pro His Asp
    130                 135                 140

Leu Asn Ile Ala Thr Trp Ala Ala Thr Val Gln Lys Thr Val Thr Ala
145                 150                 155                 160

Ile Arg Asn Thr Gly Ala Thr Ser Gln Met Ile Leu Leu Pro Gly Thr
                165                 170                 175

Asp Tyr Thr Ser Ala Ala Asn Phe Ile Glu Asn Gly Ser Gly Ala Ala
            180                 185                 190

Leu Leu Pro Val Thr Asn Pro Asp Gly Ser Thr Thr Asn Leu Ile Phe
        195                 200                 205

Asp Val His Lys Tyr Leu Asp Ser Asp Asn Ser Gly Thr His Ala Glu
    210                 215                 220

Cys Val Thr Asn Asn Ala Asp Ala Phe Asn Leu Ala Thr Trp Leu
225                 230                 235                 240

Arg Ser Asn Lys Arg Gln Ala Leu Leu Ser Glu Thr Gly Gly Gly Asn
                245                 250                 255

Val Gln Ser Cys Ala Thr Tyr Met Cys Gln Gln Leu Asp Ile Leu Asn
            260                 265                 270

Ala Asn Ser Asp Val Tyr Leu Gly Trp Thr Trp Ser Ala Gly Gly
        275                 280                 285

Phe Gln Ala Ser Trp Asn Tyr Val Leu Thr Glu Val Pro Val Asn Gly
    290                 295                 300

Val Asp Gln Tyr Leu Val Gln Gln Cys Phe Val Pro Lys Trp Lys Asn
305                 310                 315                 320

<210> SEQ ID NO 3
<211> LENGTH: 349
<212> TYPE: PRT
<213> ORGANISM: Macrophomina phaseolina

<400> SEQUENCE: 3

Ala Pro Thr Ser Thr Leu Lys Ala Ala Ala Ala Ser Lys Val Lys Phe
1               5                   10                  15

Ala Gly Val Asn Ile Ala Gly Phe Asp Phe Gly Cys Gly Thr Asp Gly
                20                  25                  30

Thr Cys Thr Gln Thr Ala Ser Thr Ala Thr Asp Pro Leu Thr Asp Ser
            35                  40                  45

Asp Gly Gln Gly Gln Met Asp His Phe Val Lys Asp Asp Lys Leu Asn
        50                  55                  60

Ala Phe Arg Leu Pro Val Gly Trp Gln Tyr Leu Val Ala Asn Lys Leu
65                  70                  75                  80

Gly Gly Asp Leu Asp Ser Ala Asn Ala Gly Lys Tyr Asp Asn Leu Val
                85                  90                  95

Gln Gly Cys Leu Lys Ser Gly Ala Glu Leu Cys Ile Ile Asp Ile His
            100                 105                 110

Asn Tyr Ala Leu Leu Glu Arg Pro Asp His Arg Gln Gly Gly Pro Thr
        115                 120                 125

Asn Asp Gln Phe Val Ser Leu Trp Lys Gln Leu Ala Thr Lys Tyr Lys
    130                 135                 140

Asp Asn Thr Lys Val Ala Phe Gly Val Met Asn Glu Pro His Asp Val
145                 150                 155                 160

Pro Asp Ile Asn Lys Trp Ala Asp Thr Val Gln Gln Val Val Thr Ala
                165                 170                 175

Ile Arg Asn Arg Gly Ala Thr Thr Gln Tyr Val Leu Leu Pro Gly Asn
            180                 185                 190
```

```
Asp Trp Thr Ser Ala Ala Ala Phe Ile Asp Asn Gly Ser Ala Ala Ala
        195                 200                 205

Leu Lys Lys Val Thr Asn Pro Asp Gly Ser Thr Asp Asn Leu Ile Phe
    210                 215                 220

Asp Val His Lys Tyr Leu Asp Ser Asp Asn Ser Gly Thr His Thr Glu
225                 230                 235                 240

Cys Val Thr Asn Asn Ile Asp Asp Ala Phe Lys Pro Leu Ala Asp Trp
                245                 250                 255

Leu Arg Gln Asn Lys Arg Met Ala Ile Asn Thr Glu Ser Gly Gly Gly
        260                 265                 270

Asn Thr Asp Ser Cys Glu Lys Tyr Phe Cys Glu Gln Ile Gln Tyr Leu
    275                 280                 285

Asn Gln Asn Ala Asp Val Phe Leu Gly Tyr Thr Ala Trp Ser Ala Gly
290                 295                 300

Gly Phe Asp Gln Thr Tyr Glu Leu Val Gln Thr Pro Ile Ser Ser Pro
305                 310                 315                 320

Met Ala Arg Thr Lys Ile Leu His Ser Arg Arg Ser Ala Leu Leu Val
                325                 330                 335

Leu Gly Arg Met Leu Glu Gly Arg His Glu Phe Met Tyr
        340                 345

<210> SEQ ID NO 4
<211> LENGTH: 323
<212> TYPE: PRT
<213> ORGANISM: Cryptococcus flavus

<400> SEQUENCE: 4

Ala Pro Leu Ala Gly Asp Ser Ala Leu His Arg Arg Ser Leu Pro Arg
1               5                   10                  15

Leu Gly Gly Val Asn Leu Ala Gly Cys Asp Phe Gly Ile Asp Ile Tyr
            20                  25                  30

Gly Asn Ser Gly Thr Pro Ala Cys Pro Gly Thr Glu Gln Val Gly His
        35                  40                  45

Phe Ile Ala Asp Gly Ala Asn Leu Phe Arg Leu Pro Ala Gly Trp Gln
    50                  55                  60

Tyr Leu Val Gly Asn Asn Gln Ala Ser Thr Ser Leu Ala Pro Asp Phe
65                  70                  75                  80

Phe Ala Gln Tyr Asp Ala Leu Val Gln Ala Val Ile Ser Lys Gly Ala
                85                  90                  95

Tyr Ala Ile Ile Asp Val His Asn Tyr Ala Arg Trp Asn Gly Ala Ile
            100                 105                 110

Ile Gly Gln Gly Gly Pro Ser Asn Gln Asp Phe Ala Asn Leu Trp Thr
        115                 120                 125

Leu Leu Ala Thr Lys Val Thr Ser Asn Asp Pro Asn Val Ile Phe Gly
    130                 135                 140

Leu Met Asn Glu Pro His Asp Leu Asp Val Ser Thr Trp Ala Gly Ser
145                 150                 155                 160

Val Gln Ala Ala Val Asn Ala Ile Arg Ala Gly Ala Thr Ser Gln
                165                 170                 175

Tyr Ile Leu Ile Pro Gly Thr Gly Phe Thr Asn Ala Asn Ala Trp Phe
            180                 185                 190

Gln Gly Gln Asp Asn Ala Leu Leu Gly Val Thr Asp Pro Val Gly Gly
        195                 200                 205

Thr Asp Lys Leu Leu Leu Asp Val His Arg Tyr Asn Asp Val Asp Phe
    210                 215                 220
```

```
Ser Gly Thr His Ala Glu Cys Thr Thr Asn Ser Leu Asp Val Leu Ser
225                 230                 235                 240

Ser Leu Asp Ser Trp Leu Lys Gly Asn Gly Arg Lys Ala Ile Val Ser
            245                 250                 255

Glu Thr Gly Gly Gly His Thr Thr Ser Cys Glu Thr Asp Leu Gly Glu
        260                 265                 270

Phe Leu Asn Gly Ile Lys Glu Asp Tyr Pro Ser Val Leu Gly Phe Ala
        275                 280                 285

Val Trp Ala Ala Gly Ser Phe Asp Pro Ser Tyr Val Leu Ser Ile Thr
    290                 295                 300

Pro Thr Asn Gly Val Asp Asn Gln Leu Phe Asp Ile Ala Val Lys Pro
305                 310                 315                 320

Asn Leu Pro

<210> SEQ ID NO 5
<211> LENGTH: 307
<212> TYPE: PRT
<213> ORGANISM: Aspergillus nidulans

<400> SEQUENCE: 5

Ala Phe Thr Trp Leu Gly Thr Asn Glu Ala Gly Ala Glu Phe Gly Glu
1               5                   10                  15

Gly Ser Tyr Pro Gly Glu Leu Gly Thr Glu Tyr Ile Trp Pro Asp Leu
            20                  25                  30

Gly Thr Ile Gly Thr Leu Arg Asn Glu Gly Met Asn Ile Phe Arg Val
        35                  40                  45

Ala Phe Ser Met Glu Arg Leu Val Pro Asp Ser Leu Ala Gly Pro Val
    50                  55                  60

Ala Asp Glu Tyr Phe Gln Asp Leu Val Glu Thr Val Asn Gly Ile Thr
65                  70                  75                  80

Ala Leu Gly Ala Tyr Ala Val Leu Asp Pro His Asn Tyr Gly Arg Tyr
                85                  90                  95

Tyr Gly Asn Ile Ile Thr Ser Thr Asp Asp Phe Ala Ala Phe Trp Thr
            100                 105                 110

Ile Leu Ala Thr Glu Phe Ala Ser Asn Glu Leu Val Ile Phe Asp Thr
        115                 120                 125

Asn Asn Glu Tyr His Thr Met Asp Gln Ser Leu Val Leu Asn Leu Asn
130                 135                 140

Gln Ala Ala Ile Asp Ala Ile Arg Ala Ser Gly Ala Thr Ser Gln Tyr
145                 150                 155                 160

Ile Phe Ala Glu Gly Asn Ser Trp Thr Gly Ala Trp Thr Trp Val Asp
                165                 170                 175

Val Asn Asp Asn Met Lys Ala Leu Thr Asp Pro Gln Asp Lys Leu Ile
            180                 185                 190

Tyr Glu Met His Gln Tyr Leu Asp Ser Asp Gly Ser Gly Thr Asn Thr
        195                 200                 205

Ala Cys Val Ser Ser Thr Ile Gly Ser Glu Arg Val Thr Ala Ala Thr
    210                 215                 220

Asn Trp Leu Arg Glu Asn Gly Lys Leu Gly Val Leu Gly Glu Phe Ala
225                 230                 235                 240

Gly Ala Asn Asn Gln Val Cys Lys Asp Ala Val Ala Asp Leu Leu Glu
                245                 250                 255

Tyr Leu Glu Glu Asn Ser Asp Val Trp Leu Gly Ala Leu Trp Trp Ala
            260                 265                 270
```

Ala Gly Pro Trp Trp Gly Asp Tyr Met Phe Asn Met Glu Pro Thr Ser
            275                 280                 285
Gly Ile Ala Tyr Gln Glu Tyr Ser Glu Ile Leu Gln Pro Tyr Phe Val
        290                 295                 300
Gly Ser Gln
305

<210> SEQ ID NO 6
<211> LENGTH: 313
<212> TYPE: PRT
<213> ORGANISM: Aspergillus kawachii

<400> SEQUENCE: 6

Leu Pro Ser Arg Gln Met Lys Lys Arg Asp Ser Gly Phe Lys Trp Val
1               5                   10                  15
Gly Thr Ser Glu Ser Gly Ala Glu Phe Gly Ser Ala Leu Pro Gly Thr
            20                  25                  30
Leu Gly Thr Asp Tyr Thr Trp Pro Glu Thr Ser Lys Ile Gln Val Leu
        35                  40                  45
Arg Asn Lys Gly Met Asn Ile Phe Arg Ile Pro Phe Leu Met Glu Arg
    50                  55                  60
Leu Thr Pro Asp Gly Leu Thr Gly Ser Phe Ala Ser Thr Tyr Leu Ser
65                  70                  75                  80
Asp Leu Lys Ser Thr Val Glu Phe Val Thr Asn Ser Gly Ala Tyr Ala
                85                  90                  95
Val Leu Asp Pro His Asn Tyr Gly Arg Phe Asp Gly Ser Ile Ile Glu
            100                 105                 110
Ser Thr Ser Asp Phe Lys Thr Trp Trp Lys Asn Val Ala Thr Glu Phe
        115                 120                 125
Ala Asp Asn Asp Lys Val Ile Phe Asp Thr Asn Asn Glu Tyr His Asp
    130                 135                 140
Met Glu Gln Ser Leu Val Leu Asn Leu Asn Gln Ala Ala Ile Asn Gly
145                 150                 155                 160
Ile Arg Ala Ala Gly Ala Thr Thr Gln Tyr Ile Phe Val Glu Gly Asn
                165                 170                 175
Ala Tyr Thr Gly Ala Trp Asp Trp Thr Thr Tyr Asn Asp Asp Leu Ser
            180                 185                 190
Gly Leu Thr Asp Ser Glu Asp Lys Ile Ile Tyr Glu Met His Gln Tyr
        195                 200                 205
Leu Asp Ser Asp Ser Ser Gly Thr Ser Glu Thr Cys Val Ser Ser Thr
    210                 215                 220
Ile Gly Lys Glu Arg Ile Glu Lys Ala Thr Glu Trp Leu Lys Thr Asn
225                 230                 235                 240
Asn Lys Gln Gly Ile Ile Gly Glu Phe Ala Gly Val Asn Ser Val
                245                 250                 255
Cys Glu Glu Ala Val Glu Gly Met Leu Ala Tyr Met Ser Glu Asn Ser
            260                 265                 270
Asp Val Trp Val Gly Ala Ser Trp Trp Ser Ala Gly Pro Trp Trp Gly
        275                 280                 285
Thr Tyr Met Tyr Ser Leu Glu Pro Thr Asp Gly Thr Ala Tyr Ser Thr
    290                 295                 300
Tyr Leu Pro Ile Leu Glu Lys Tyr Phe
305                 310

<210> SEQ ID NO 7
<211> LENGTH: 307

<212> TYPE: PRT
<213> ORGANISM: Macrophomina phaseolina

<400> SEQUENCE: 7

```
Ala Ser Asn Phe Gln Phe Phe Gly Val Asn Glu Ser Gly Pro Glu Phe
1               5                   10                  15

Gly Glu Thr Lys Leu Pro Gly Thr Lys Asn Thr Asp Tyr Val Trp Pro
            20                  25                  30

Thr Leu Ser Thr Ile Asp Thr Phe Val Gly Lys Gly Met Asn Thr Phe
        35                  40                  45

Arg Val Asn Ile Leu Met Glu Arg Leu Thr His Asn Ser Leu Thr Ala
    50                  55                  60

Ser Leu Asp Ser Gln Tyr Leu Ala Asp Leu Lys Thr Thr Val Asn Tyr
65                  70                  75                  80

Ile Thr Gly Lys Gly Ala Tyr Ala Met Ile Val Pro His Asn Tyr Gly
                85                  90                  95

Arg Phe Asn Ser Gln Ile Ile Thr Asp Thr Ala Gly Phe Lys Thr Trp
            100                 105                 110

Trp Thr Asn Val Ala Lys Glu Phe Ala Gly Asn Ser Lys Val Ile Phe
        115                 120                 125

Asp Ile Asn Asn Glu Phe His Asp Met Asp Gln Thr Leu Val Val Asn
    130                 135                 140

Leu Asn Gln Ala Gly Ile Asp Gly Ile Arg Ala Ala Gly Ala Thr Ser
145                 150                 155                 160

Gln Tyr Ile Thr Ala Glu Gly Asn Ser Trp Thr Gly Ala Trp Thr Trp
                165                 170                 175

Thr Thr Ser Glu Asn Gly Lys Thr Met Ala Ala Leu Lys Asp Pro Gln
            180                 185                 190

Asn Lys Leu Ile Tyr Gln Met His Gln Tyr Leu Asp Ser Asp Gly Ser
        195                 200                 205

Gly Thr Asn Glu Ala Cys Val Ser Ser Thr Ile Gly Lys Glu Arg Ile
    210                 215                 220

Thr Ala Ala Thr Lys Trp Leu Lys Asp Asn Gly Lys Lys Gly Leu Ile
225                 230                 235                 240

Gly Glu Phe Ala Gly Gly Asn Asn Ser Gln Cys Lys Thr Ala Val Glu
                245                 250                 255

Gly Met Leu Thr Tyr Met Gln Glu Asn Lys Asp Val Trp Thr Gly Ala
            260                 265                 270

Leu Trp Trp Ala Ala Gly Pro Trp Trp Ala Ser Tyr Met Phe Ser Met
        275                 280                 285

Glu Pro Lys Thr Gly Thr Ala Tyr Thr Ala Tyr Leu Asp Leu Ile Ser
    290                 295                 300

Lys Phe Lys
305
```

<210> SEQ ID NO 8
<211> LENGTH: 309
<212> TYPE: PRT
<213> ORGANISM: Volvariella volvacea

<400> SEQUENCE: 8

```
Ala Thr Lys Phe Arg Phe Phe Gly Val Asn Gln Ala Gly Ala Glu Phe
1               5                   10                  15

Gly Glu Asn Val Ile Pro Gly Glu Leu Gly Thr His Tyr Thr Trp Pro
            20                  25                  30

Ser Pro Ser Ser Ile Asp Tyr Phe Val Asn Gln Gly Phe Asn Thr Phe
```

```
                   35                  40                  45
Arg Val Ala Phe Lys Ile Glu Arg Leu Ser Pro Pro Gly Thr Gly Leu
        50                  55                  60

Thr Gly Pro Phe Asp Gln Ala Tyr Leu Asn Gly Leu Lys Thr Ile Val
65                  70                  75                  80

Asn Tyr Ile Thr Gly Lys Asn Ala Tyr Ala Val Leu Asp Pro His Asn
                85                  90                  95

Tyr Met Arg Tyr Asn Gly Asn Val Ile Thr Ser Thr Ser Asn Phe Gln
                    100                 105                 110

Thr Trp Trp Asn Lys Leu Ala Thr Glu Phe Arg Ser Asn Thr Arg Val
                115                 120                 125

Ile Phe Asp Val Met Asn Glu Pro Tyr Gln Ile Asp Ala Ser Val Val
                130                 135                 140

Phe Asn Leu Asn Gln Ala Ala Ile Asn Gly Ile Arg Ala Ser Gly Ala
145                 150                 155                 160

Thr Ser Gln Leu Ile Leu Val Glu Gly Thr Ala Trp Thr Gly Ala Trp
                165                 170                 175

Ser Trp Glu Ser Ser Gly Asn Gly Ala Val Phe Gly Ala Ile Arg Asp
                180                 185                 190

Pro Asn Asn Asn Thr Ala Ile Glu Met His Gln Tyr Leu Asp Ser Asp
                195                 200                 205

Ser Ser Gly Thr Ser Ala Thr Cys Val Ser Ser Thr Val Gly Val Glu
                210                 215                 220

Arg Leu Arg Val Ala Thr Asp Trp Leu Arg Arg Asn Asn Leu Lys Gly
225                 230                 235                 240

Phe Leu Gly Glu Met Gly Ala Gly Ser Asn Asp Val Cys Ile Ala Ala
                245                 250                 255

Val Lys Gly Ala Leu Cys Ala Met Gln Gln Ser Gly Val Trp Ile Gly
                260                 265                 270

Tyr Leu Trp Trp Ala Ala Gly Pro Trp Trp Gly Thr Tyr Phe Gln Ser
                275                 280                 285

Ile Glu Pro Pro Asn Gly Ala Ser Ile Ala Arg Ile Leu Pro Glu Ala
        290                 295                 300

Leu Lys Pro Phe Val
305

<210> SEQ ID NO 9
<211> LENGTH: 305
<212> TYPE: PRT
<213> ORGANISM: Thermoascus aurantiacus

<400> SEQUENCE: 9

Ala Lys Val Phe Gln Trp Phe Gly Ser Asn Glu Ser Gly Ala Glu Phe
1               5                   10                  15

Gly Ser Gln Asn Leu Pro Gly Val Glu Gly Lys Asp Tyr Ile Trp Pro
                20                  25                  30

Asp Pro Asn Thr Ile Asp Thr Leu Ile Ser Lys Gly Met Asn Ile Phe
            35                  40                  45

Arg Val Pro Phe Met Met Glu Arg Leu Val Pro Asn Ser Met Thr Gly
        50                  55                  60

Ser Pro Asp Pro Asn Tyr Leu Ala Asp Leu Ile Ala Thr Val Asn Ala
65                  70                  75                  80

Ile Thr Gln Lys Gly Ala Tyr Ala Val Val Asp Pro His Asn Tyr Gly
                85                  90                  95

Arg Tyr Tyr Asn Ser Ile Ile Ser Ser Pro Ser Asp Phe Gln Thr Phe
```

```
                100                 105                 110
Trp Lys Thr Val Ala Ser Gln Phe Ala Ser Asn Pro Leu Val Ile Phe
            115                 120                 125

Asp Thr Asn Asn Glu Tyr His Asp Met Asp Gln Thr Leu Val Leu Asn
130                 135                 140

Leu Asn Gln Ala Ala Ile Asp Gly Ile Arg Ser Ala Gly Ala Thr Ser
145                 150                 155                 160

Gln Tyr Ile Phe Val Glu Gly Asn Ser Trp Thr Gly Ala Trp Thr Trp
                165                 170                 175

Thr Asn Val Asn Asp Asn Met Lys Ser Leu Thr Asp Pro Ser Asp Lys
            180                 185                 190

Ile Ile Tyr Glu Met His Gln Tyr Leu Asp Ser Asp Gly Ser Gly Thr
        195                 200                 205

Ser Ala Thr Cys Val Ser Ser Thr Ile Gly Gln Glu Arg Ile Thr Ser
    210                 215                 220

Ala Thr Gln Trp Leu Arg Ala Asn Gly Lys Lys Gly Ile Ile Gly Glu
225                 230                 235                 240

Phe Ala Gly Gly Ala Asn Asp Val Cys Glu Thr Ala Ile Thr Gly Met
                245                 250                 255

Leu Asp Tyr Met Ala Gln Asn Thr Asp Val Trp Thr Gly Ala Ile Trp
            260                 265                 270

Trp Ala Ala Gly Pro Trp Trp Gly Asp Tyr Ile Phe Ser Met Glu Pro
        275                 280                 285

Asp Asn Gly Ile Ala Tyr Gln Gln Ile Leu Pro Ile Leu Thr Pro Tyr
    290                 295                 300

Leu
305

<210> SEQ ID NO 10
<211> LENGTH: 305
<212> TYPE: PRT
<213> ORGANISM: Aspergillus aculeatus

<400> SEQUENCE: 10

Ala Ser Val Phe Glu Trp Ile Gly Ser Asn Glu Ser Asp Ala Glu Phe
1               5                   10                  15

Gly Thr Ala Ile Pro Gly Thr Trp Gly Ile Asp Tyr Ile Phe Pro Asp
            20                  25                  30

Thr Ser Ala Ile Ala Thr Leu Val Ser Lys Gly Met Asn Ile Phe Arg
        35                  40                  45

Val Gln Phe Met Met Glu Arg Leu Val Pro Asn Ser Met Thr Gly Ser
50                  55                  60

Tyr Asp Asp Ala Tyr Leu Asn Asn Leu Thr Thr Val Val Asn Ala Ile
65                  70                  75                  80

Ala Ala Ala Gly Val His Ala Ile Val Asp Pro His Asn Tyr Gly Arg
                85                  90                  95

Tyr Asn Asn Glu Ile Ile Ser Ser Thr Ala Asp Phe Gln Thr Phe Trp
            100                 105                 110

Gln Asn Leu Ala Gly Gln Phe Lys Asp Asn Asp Leu Val Ile Phe Asp
        115                 120                 125

Thr Asn Asn Glu Tyr Asn Thr Met Asp Gln Thr Leu Val Leu Asp Leu
    130                 135                 140

Asn Gln Ala Ala Ile Asp Gly Ile Arg Ala Ala Gly Ala Thr Ser Gln
145                 150                 155                 160

Tyr Ile Phe Ala Glu Gly Asn Ser Trp Ser Gly Ala Trp Thr Trp Ala
```

```
                       165                 170                 175
Asp Ile Asn Asp Asn Met Lys Ala Leu Thr Asp Pro Gln Asp Lys Leu
            180                 185                 190

Val Tyr Glu Met His Gln Tyr Leu Asp Ser Asp Gly Ser Gly Thr Ser
        195                 200                 205

Gly Val Cys Val Ser Glu Thr Ile Gly Ala Glu Arg Leu Gln Ala Ala
    210                 215                 220

Thr Gln Trp Leu Lys Asp Asn Gly Lys Val Asp Ile Leu Gly Glu Tyr
225                 230                 235                 240

Ala Gly Gly Ala Asn Asp Val Cys Arg Thr Ala Ile Ala Gly Met Leu
                245                 250                 255

Glu Tyr Met Ala Asn Asn Thr Asp Val Trp Lys Gly Ala Val Trp Trp
            260                 265                 270

Thr Ala Gly Pro Trp Trp Ala Asp Tyr Met Phe Ser Met Glu Pro Pro
        275                 280                 285

Ser Gly Pro Ala Tyr Ser Gly Met Leu Asp Val Leu Glu Pro Tyr Leu
    290                 295                 300

Gly
305

<210> SEQ ID NO 11
<211> LENGTH: 306
<212> TYPE: PRT
<213> ORGANISM: Humicola insolens

<400> SEQUENCE: 11

Lys Gly Lys Phe Lys Trp Phe Gly Ile Asn Gln Ser Cys Ala Glu Phe
1               5                   10                  15

Gly Lys Gly Glu Tyr Pro Gly Leu Trp Gly Lys His Phe Thr Phe Pro
            20                  25                  30

Ser Thr Ser Ser Ile Gln Thr His Ile Asn Asp Gly Phe Asn Met Phe
        35                  40                  45

Arg Val Ala Phe Ser Met Glu Arg Leu Ala Pro Asn Gln Leu Asn Ala
    50                  55                  60

Ala Phe Asp Ala Asn Tyr Leu Arg Asn Leu Thr Glu Thr Val Asn Phe
65                  70                  75                  80

Ile Thr Gly Lys Gly Lys Tyr Ala Met Leu Asp Pro His Asn Phe Gly
                85                  90                  95

Arg Tyr Tyr Glu Arg Ile Ile Thr Asp Lys Ala Ala Phe Ala Ser Phe
            100                 105                 110

Phe Thr Lys Leu Ala Thr His Phe Ala Ser Asn Pro Leu Val Val Phe
        115                 120                 125

Asp Thr Asn Asn Glu Tyr His Asp Met Asp Gln Gln Leu Val Phe Asp
    130                 135                 140

Leu Asn Gln Ala Ala Ile Asp Ala Ile Arg Ala Ala Gly Ala Thr Ser
145                 150                 155                 160

Gln Tyr Ile Met Val Glu Gly Asn Ser Trp Thr Gly Ala Trp Thr Trp
                165                 170                 175

Asn Val Thr Asn Asn Asn Leu Ala Ala Leu Arg Asp Pro Glu Asn Lys
            180                 185                 190

Leu Val Tyr Gln Met His Gln Tyr Leu Asp Ser Asp Gly Ser Gly Thr
        195                 200                 205

Ser Thr Ala Cys Val Ser Thr Gln Val Gly Leu Gln Arg Val Ile Gly
    210                 215                 220

Ala Thr Asn Trp Leu Arg Gln Asn Gly Lys Val Gly Leu Leu Gly Glu
```

```
                225                 230                 235                 240
Phe Ala Gly Gly Ala Asn Ser Val Cys Gln Gln Ala Ile Glu Gly Met
                    245                 250                 255
Leu Thr His Leu Gln Glu Asn Ser Asp Val Trp Thr Gly Ala Leu Trp
                260                 265                 270
Trp Ala Gly Gly Pro Trp Trp Gly Asp Tyr Ile Tyr Ser Phe Glu Pro
            275                 280                 285
Pro Ser Gly Ile Gly Tyr Thr Tyr Tyr Asn Ser Leu Leu Lys Lys Tyr
        290                 295                 300
Val Pro
305

<210> SEQ ID NO 12
<211> LENGTH: 351
<212> TYPE: PRT
<213> ORGANISM: Orpinomyces joyonii

<400> SEQUENCE: 12

Met Arg Asn Ile Pro Ser Lys Asp Leu Val Lys Glu Leu Asn Ile Gly
1               5                   10                  15
Trp Asn Leu Gly Asn Ala Leu Asp Ala His Cys Leu Asp Lys Leu Asp
                20                  25                  30
Tyr Asn Lys Asp Gln Leu Ala Ser Glu Thr Cys Trp Ala Asn Pro Lys
            35                  40                  45
Ala Thr Pro Gly Leu Phe Ser Ala Leu Lys Asn Gln Gly Phe Asn Val
        50                  55                  60
Phe Arg Ile Pro Thr Thr Trp Thr Gly His Phe Gly Asn Gly Pro Asp
65                  70                  75                  80
Tyr Lys Ile Ser Asp Val Trp Met Arg Arg Val His Glu Val Val Asp
                85                  90                  95
Tyr Ala Leu Asn Thr Gly Ser Tyr Val Ile Leu Asn Ile His His Glu
            100                 105                 110
Asn Trp Asn Tyr Ala Phe Ser Asn Asn Leu Gln Lys Ala Lys Pro Ile
        115                 120                 125
Leu Ala Ala Ile Trp Lys Gln Ile Ala Ala Glu Phe Ala Asn Tyr Asp
    130                 135                 140
Glu His Leu Ile Phe Glu Gly Met Asn Glu Pro Arg Lys Val Asp His
145                 150                 155                 160
Pro Asn Glu Trp Asn Gly Gly Asp Gln Lys Gly Trp Asp Phe Val Asn
                165                 170                 175
Glu Met Asn Ala Val Phe Leu Gln Thr Val Arg Ala Ser Gly Gly Asn
            180                 185                 190
Asn Ala Ile Arg His Leu Met Ile Pro Thr Tyr Ala Ala Cys Val Asn
        195                 200                 205
Asn Gly Ala Leu Glu Ser Tyr Phe Lys Lys Ser Pro Thr Asn Asp Asn
    210                 215                 220
Lys Val Ile Ala Ser Val His Ser Tyr Val Pro Tyr Asn Phe Ala Leu
225                 230                 235                 240
Asn Thr Gly Ala Gly Ala Glu Lys Thr Phe Gly Ser Thr Ser Asp Ile
                245                 250                 255
Glu Trp Ala Met Asn Asn Ile Lys Arg Phe Leu Val Asp Arg Asn Ile
            260                 265                 270
Pro Val Ile Ile Gly Glu Phe Gly Ala Met Asn Arg Asp Asn Glu Ser
        275                 280                 285
Glu Arg Ala Arg Trp Ala Glu Tyr Tyr Ile Lys Ser Ala Thr Ala Met
```

```
            290                 295                 300
Gly Val Pro Cys Val Leu Trp Asp Asn Gly Tyr Thr Gln Gly Thr Gly
305                 310                 315                 320

Glu Leu Phe Gly Val Ile Asp Arg Asn Phe Tyr Arg Ile Ile Phe Gln
                325                 330                 335

Gln Phe Ile Asn Gly Leu Met Lys Gly Leu Gly Gly Lys Lys Thr
            340                 345                 350

<210> SEQ ID NO 13
<211> LENGTH: 358
<212> TYPE: PRT
<213> ORGANISM: Acidothermus cellulolyticus

<400> SEQUENCE: 13

Ala Gly Gly Gly Tyr Trp His Thr Ser Gly Arg Glu Ile Leu Asp Ala
1               5                   10                  15

Asn Asn Val Pro Val Arg Ile Ala Gly Ile Asn Trp Phe Gly Phe Glu
                20                  25                  30

Thr Cys Asn Tyr Val Val His Gly Leu Trp Ser Arg Asp Tyr Arg Ser
            35                  40                  45

Met Leu Asp Gln Ile Lys Ser Leu Gly Tyr Asn Thr Ile Arg Leu Pro
50                  55                  60

Tyr Ser Asp Asp Ile Leu Lys Pro Gly Thr Met Pro Asn Ser Ile Asn
65                  70                  75                  80

Phe Tyr Gln Met Asn Gln Asp Leu Gln Gly Leu Thr Ser Leu Gln Val
                85                  90                  95

Met Asp Lys Ile Val Ala Tyr Ala Gly Gln Ile Gly Leu Arg Ile Ile
            100                 105                 110

Leu Asp Arg His Arg Pro Asp Cys Ser Gly Gln Ser Ala Leu Trp Tyr
            115                 120                 125

Thr Ser Ser Val Ser Glu Ala Thr Trp Ile Ser Asp Leu Gln Ala Leu
130                 135                 140

Ala Gln Arg Tyr Lys Gly Asn Pro Thr Val Val Gly Phe Asp Leu His
145                 150                 155                 160

Asn Glu Pro His Asp Pro Ala Cys Trp Gly Cys Gly Asp Pro Ser Ile
                165                 170                 175

Asp Trp Arg Leu Ala Ala Glu Arg Ala Gly Asn Ala Val Leu Ser Val
            180                 185                 190

Asn Pro Asn Leu Leu Ile Phe Val Glu Gly Val Gln Ser Tyr Asn Gly
            195                 200                 205

Asp Ser Tyr Trp Trp Gly Gly Asn Leu Gln Gly Ala Gly Gln Tyr Pro
210                 215                 220

Val Val Leu Asn Val Pro Asn Arg Leu Val Tyr Ser Ala His Asp Tyr
225                 230                 235                 240

Ala Thr Ser Val Tyr Pro Gln Thr Trp Phe Ser Asp Pro Thr Phe Pro
                245                 250                 255

Asn Asn Met Pro Gly Ile Trp Asn Lys Asn Trp Gly Tyr Leu Phe Asn
            260                 265                 270

Gln Asn Ile Ala Pro Val Trp Leu Gly Glu Phe Gly Thr Thr Leu Gln
            275                 280                 285

Ser Thr Thr Asp Gln Thr Trp Leu Lys Thr Leu Val Gln Tyr Leu Arg
            290                 295                 300

Pro Thr Ala Gln Tyr Gly Ala Asp Ser Phe Gln Trp Thr Phe Trp Ser
305                 310                 315                 320

Trp Asn Pro Asp Ser Gly Asp Thr Gly Gly Ile Leu Lys Asp Asp Trp
```

```
                    325                 330                 335
Gln Thr Val Asp Thr Val Lys Asp Gly Tyr Leu Ala Pro Ile Lys Ser
                340                 345                 350

Ser Ile Phe Asp Pro Val
            355

<210> SEQ ID NO 14
<211> LENGTH: 312
<212> TYPE: PRT
<213> ORGANISM: Bacillus subtilis

<400> SEQUENCE: 14

Ala Gly Thr Lys Thr Pro Val Ala Lys Asn Gly Gln Leu Ser Ile Lys
1               5                   10                  15

Gly Thr Gln Leu Val Asn Arg Asp Gly Lys Ala Val Gln Leu Lys Gly
                20                  25                  30

Ile Ser Ser His Gly Leu Gln Trp Tyr Gly Glu Phe Val Asn Lys Asp
            35                  40                  45

Ser Leu Lys Trp Leu Arg Asp Asp Trp Gly Ile Thr Val Phe Arg Ala
        50                  55                  60

Ala Met Tyr Thr Ala Asp Gly Gly Tyr Ile Asp Asn Pro Ser Val Lys
65                  70                  75                  80

Asn Lys Val Lys Glu Ala Val Glu Ala Ala Lys Glu Leu Gly Ile Tyr
                85                  90                  95

Val Ile Ile Asp Trp His Ile Leu Asn Asp Gly Asn Pro Asn Gln Asn
            100                 105                 110

Lys Glu Lys Ala Lys Glu Phe Phe Lys Glu Met Ser Ser Leu Tyr Gly
        115                 120                 125

Asn Thr Pro Asn Val Ile Tyr Glu Ile Ala Asn Glu Pro Asn Gly Asp
130                 135                 140

Val Asn Trp Lys Arg Asp Ile Lys Pro Tyr Ala Glu Glu Val Ile Ser
145                 150                 155                 160

Val Ile Arg Lys Asn Asp Pro Asp Asn Ile Ile Ile Val Gly Thr Gly
                165                 170                 175

Thr Trp Ser Gln Asp Val Asn Asp Ala Ala Asp Asp Gln Leu Lys Asp
            180                 185                 190

Ala Asn Val Met Tyr Ala Leu His Phe Tyr Ala Gly Thr His Gly Gln
        195                 200                 205

Phe Leu Arg Asp Lys Ala Asn Tyr Ala Leu Ser Lys Gly Ala Pro Val
    210                 215                 220

Phe Val Thr Glu Trp Gly Thr Ser Asp Ala Ser Gly Asn Gly Gly Val
225                 230                 235                 240

Phe Leu Asp Gln Ser Arg Glu Trp Leu Asn Tyr Leu Asp Ser Lys Thr
                245                 250                 255

Ile Ser Trp Val Asn Trp Asn Leu Ser Asp Lys Gln Glu Ser Ser Ser
            260                 265                 270

Ala Leu Lys Pro Gly Ala Ser Lys Thr Gly Gly Trp Arg Leu Ser Asp
        275                 280                 285

Leu Ser Ala Ser Gly Thr Phe Val Arg Glu Asn Ile Leu Gly Thr Lys
    290                 295                 300

Asp Ser Thr Lys Asp Ile Pro Glu
305                 310

<210> SEQ ID NO 15
<211> LENGTH: 302
<212> TYPE: PRT
```

<213> ORGANISM: Bacillus cellulosilyticus

<400> SEQUENCE: 15

```
Asp Asp Tyr Ser Val Glu Glu His Gly Gln Leu Ser Ile Ser Asn
1               5                   10                  15

Gly Glu Leu Val Asn Asp Arg Gly Glu Pro Val Gln Leu Lys Gly Met
                20                  25                  30

Ser Ser His Gly Leu Gln Trp Tyr Gly Gln Phe Val Asn Tyr Glu Ser
            35                  40                  45

Met Lys Trp Leu Arg Asp Asp Trp Gly Ile Thr Val Phe Arg Ala Ala
    50                  55                  60

Met Tyr Thr Ser Ser Gly Gly Tyr Ile Glu Asp Pro Ser Val Lys Glu
65                  70                  75                  80

Lys Val Lys Glu Ala Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asn Asn Asp Pro Asn Asn Ile Ile Ile Val Gly Thr Gly
                165                 170                 175

Thr Trp Ser Gln Asp Val His His Ala Ala Asp Asn Gln Leu Thr Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220

Phe Val Ser Glu Trp Gly Thr Ser Glu Ala Thr Gly Asp Gly Gly Val
225                 230                 235                 240

Phe Leu Asp Glu Ala Gln Val Trp Ile Asp Phe Met Asp Glu Arg Asn
                245                 250                 255

Leu Ser Trp Ala Asn Trp Ser Leu Thr His Lys Asp Glu Ser Ser Ala
            260                 265                 270

Ala Leu Met Pro Gly Ala Ser Pro Thr Gly Gly Trp Thr Glu Ala Glu
        275                 280                 285

Leu Ser Pro Ser Gly Thr Phe Val Arg Glu Lys Ile Arg Glu
    290                 295                 300
```

<210> SEQ ID NO 16
<211> LENGTH: 303
<212> TYPE: PRT
<213> ORGANISM: Artificial
<220> FEATURE:
<223> OTHER INFORMATION: Alignment consensus sequence

<400> SEQUENCE: 16

```
Ala Ser Lys Phe Arg Trp Phe Gly Val Asn Ile Ala Gly Ala Glu Phe
1               5                   10                  15

Gly Glu Thr Thr Asp Pro Gly Val Gln Gly Thr Asp Tyr Ser Trp Pro
                20                  25                  30

Gly Thr Ser Gln Ile Asp Thr Phe Val Asn Asp Gly Met Asn Ile Phe
            35                  40                  45
```

Arg Val Pro Phe Gly Met Glu Arg Leu Val Pro Asn Ser Leu Thr Gly
        50                  55                  60

Ser Leu Asp Ser Thr Tyr Leu Asn Lys Leu Lys Glu Thr Val Asn Ala
 65                  70                  75                  80

Ile Thr Gly Lys Gly Ala Tyr Ala Ile Leu Asp Pro His Asn Tyr Gly
                 85                  90                  95

Arg Tyr Asn Gly Asn Ile Ile Thr Ser Thr Ala Asp Phe Ala Ser Phe
                100                 105                 110

Trp Thr Gln Leu Ala Thr Glu Phe Ala Ser Asn Pro Leu Val Ile Phe
            115                 120                 125

Asp Ile Met Asn Glu Pro His Asp Met Asp Gln Ser Leu Val Ala Asn
130                 135                 140

Leu Asn Gln Ala Ala Ile Asp Ala Ile Arg Ala Ala Gly Ala Thr Ser
145                 150                 155                 160

Gln Tyr Ile Phe Val Glu Gly Asn Ser Trp Thr Gly Ala Trp Thr Trp
                165                 170                 175

Ile Val Asn Asn Asp Ala Leu Lys Ala Leu Thr Asp Pro Asp Asn Lys
                180                 185                 190

Leu Ile Tyr Glu Met His Gln Tyr Leu Asp Ser Asp Gly Ser Gly Thr
            195                 200                 205

His Ala Glu Cys Val Ser Asn Thr Ile Gly Arg Phe Thr Asn Ala Thr
210                 215                 220

Thr Trp Leu Arg Gln Asn Gly Lys Lys Gly Ile Leu Gly Glu Phe Gly
225                 230                 235                 240

Gly Gly Asn Asn Ser Val Cys Glu Thr Ala Val Cys Gly Met Leu Gln
                245                 250                 255

Tyr Leu Asn Glu Asn Ser Asp Val Trp Leu Gly Ala Val Trp Trp Ala
                260                 265                 270

Ala Gly Pro Trp Trp Gly Thr Tyr Met Leu Ser Met Glu Pro Thr Ser
            275                 280                 285

Gly Thr Ala Tyr Gln Thr Tyr Leu Asp Leu Leu Ser Lys Tyr Leu
        290                 295                 300

<210> SEQ ID NO 17
<211> LENGTH: 397
<212> TYPE: PRT
<213> ORGANISM: Trichoderma reesei

<400> SEQUENCE: 17

Gln Gln Thr Val Trp Gly Gln Cys Gly Gly Ile Gly Trp Ser Gly Pro
 1               5                  10                  15

Thr Asn Cys Ala Pro Gly Ser Ala Cys Ser Thr Leu Asn Pro Tyr Tyr
                20                  25                  30

Ala Gln Cys Ile Pro Gly Ala Thr Thr Ile Thr Thr Ser Thr Arg Pro
             35                  40                  45

Pro Ser Gly Pro Thr Thr Thr Arg Ala Thr Ser Thr Ser Ser Ser Ser
         50                  55                  60

Thr Pro Pro Thr Ser Ser Gly Val Arg Phe Ala Gly Val Asn Ile Ala
 65                  70                  75                  80

Gly Phe Asp Phe Gly Cys Thr Thr Asp Gly Thr Cys Val Thr Ser Lys
                 85                  90                  95

Val Tyr Pro Pro Leu Lys Asn Phe Thr Gly Ser Asn Asn Tyr Pro Asp
                100                 105                 110

Gly Ile Gly Gln Met Gln His Phe Val Asn Asp Asp Gly Met Thr Ile
            115                 120                 125

Phe Arg Leu Pro Val Gly Trp Gln Tyr Leu Val Asn Asn Asn Leu Gly
            130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Gly Ile Ile Gly Gln Gly Gly Pro Thr Asn Ala
            180                 185                 190

Gln Phe Thr Ser Leu Trp Ser Gln Leu Ala Ser Lys Tyr Ala Ser Gln
        195                 200                 205

Ser Arg Val Trp Phe Gly Ile Met Asn Glu Pro His Asp Val Asn Ile
    210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
    290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Ala Ala Gly Ser Phe Asp
        355                 360                 365

Ser Thr Tyr Val Leu Thr Glu Thr Pro Thr Gly Ser Gly Asn Ser Trp
    370                 375                 380

Thr Asp Thr Ser Leu Val Ser Ser Cys Leu Ala Arg Lys
385                 390                 395

<210> SEQ ID NO 18
<211> LENGTH: 397
<212> TYPE: PRT
<213> ORGANISM: Trichoderma reesei

<400> SEQUENCE: 18

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile Pro Gly Ala Thr Thr Ile Thr Thr Ser Thr Arg Pro
        35                  40                  45

Pro Ser Gly Pro Thr Thr Thr Thr Arg Ala Ser Thr Ser Ser Ser
    50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

Val Tyr Pro Pro Leu Lys Asn Phe Thr Gly Ser Asn Asn Tyr Pro Asp
            100                 105                 110

-continued

Gly Ile Gly Gln Met Gln His Phe Val Asn Asp Asp Gly Met Thr Ile
            115                 120                 125

Phe Arg Leu Pro Val Gly Trp Gln Tyr Leu Val Asn Asn Leu Gly
130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Gly Ile Ile Gly Gln Gly Gly Pro Thr Asn Ala
            180                 185                 190

Gln Phe Thr Ser Leu Trp Ser Gln Leu Ala Ser Lys Tyr Ala Ser Gln
        195                 200                 205

Ser Arg Val Trp Phe Gly Ile Met Asn Glu Pro His Asp Val Asn Ile
    210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
    290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Ser Ala Gly Ser Phe Asp
        355                 360                 365

Ser Thr Tyr Val Leu Thr Glu Thr Pro Thr Gly Ser Gly Asn Ser Trp
    370                 375                 380

Thr Asp Thr Ser Leu Val Ser Ser Cys Leu Ala Arg Lys
385                 390                 395

<210> SEQ ID NO 19
<211> LENGTH: 397
<212> TYPE: PRT
<213> ORGANISM: Trichoderma reesei

<400> SEQUENCE: 19

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile Pro Gly Ala Thr Thr Ile Thr Ser Thr Arg Pro
        35                  40                  45

Pro Ser Gly Pro Thr Thr Thr Arg Ala Thr Ser Thr Ser Ser
    50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

```
Val Tyr Pro Pro Leu Lys Asn Phe Thr Gly Ser Asn Asn Tyr Pro Asp
            100                 105                 110

Gly Ile Gly Gln Met Gln His Phe Val Asn Asp Asp Gly Met Thr Ile
        115                 120                 125

Phe Arg Leu Pro Val Gly Trp Gln Tyr Leu Val Asn Asn Asn Leu Gly
130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Ile Ile Gly Gln Gly Pro Thr Asn Ala
                180                 185                 190

Gln Phe Thr Ser Leu Trp Ser Gln Leu Ala Ser Lys Tyr Ala Ser Gln
            195                 200                 205

Ser Arg Val Trp Phe Gly Ile Met Asn Glu Pro His Asp Val Asn Ile
        210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Thr Ala Gly Ser Phe Asp
        355                 360                 365

Ser Thr Tyr Val Leu Thr Glu Thr Pro Thr Gly Ser Gly Asn Ser Trp
370                 375                 380

Thr Asp Thr Ser Leu Val Ser Ser Cys Leu Ala Arg Lys
385                 390                 395
```

<210> SEQ ID NO 20
<211> LENGTH: 28
<212> TYPE: DNA
<213> ORGANISM: Artificial
<220> FEATURE:
<223> OTHER INFORMATION: Primer sequence

<400> SEQUENCE: 20
gagctagcac tgtctggggc cagtgtgg                                    28

<210> SEQ ID NO 21
<211> LENGTH: 34
<212> TYPE: DNA
<213> ORGANISM: Artificial
<220> FEATURE:
<223> OTHER INFORMATION: Primer sequence

<400> SEQUENCE: 21
ggtaacgcaa gtgccatctg tggtacagcc aaag                             34

```
<210> SEQ ID NO 22
<211> LENGTH: 16
<212> TYPE: DNA
<213> ORGANISM: Artificial
<220> FEATURE:
<223> OTHER INFORMATION: Primer sequence

<400> SEQUENCE: 22
tggcacttgc gttacc                                                    16

<210> SEQ ID NO 23
<211> LENGTH: 30
<212> TYPE: DNA
<213> ORGANISM: Artificial
<220> FEATURE:
<223> OTHER INFORMATION: Primer sequence

<400> SEQUENCE: 23
gaggtaccct actttcttgc gagacacgag                                     30

<210> SEQ ID NO 24
<211> LENGTH: 31
<212> TYPE: DNA
<213> ORGANISM: Artificial
<220> FEATURE:
<223> OTHER INFORMATION: Primer sequence

<400> SEQUENCE: 24
gatcgtcgac atggtctcct tcacctccct c                                   31

<210> SEQ ID NO 25
<211> LENGTH: 27
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (14)..(15)
<223> OTHER INFORMATION: n is a, c, g, or t

<400> SEQUENCE: 25
aaatgatccg gcvnnccaac caacata                                        27

<210> SEQ ID NO 26
<211> LENGTH: 27
<212> TYPE: DNA
<213> ORGANISM: Artificial
<220> FEATURE:
<223> OTHER INFORMATION: Primer sequence
<220> FEATURE:
<221> NAME/KEY: misc_feature
<222> LOCATION: (13)..(14)
<223> OTHER INFORMATION: n is a, c, g, or t

<400> SEQUENCE: 26
tatgttggtt ggnnbgccgg atcattt                                        27

<210> SEQ ID NO 27
<211> LENGTH: 23
<212> TYPE: DNA
<213> ORGANISM: Artificial
<220> FEATURE:
<223> OTHER INFORMATION: Primer sequence

<400> SEQUENCE: 27
gcaacacctg gcaattcctt acc                                            23
```

```
<210> SEQ ID NO 28
<211> LENGTH: 21
<212> TYPE: DNA
<213> ORGANISM: Artificial
<220> FEATURE:
<223> OTHER INFORMATION: Primer sequence

<400> SEQUENCE: 28
ggaaccacac catcgcacat c                                              21
```

MODIFIED FAMILY 5 CELLULASES AND USES THEREOF

FIELD OF THE INVENTION

The present invention relates to a modified cellulase enzyme and uses thereof, in particular to a modified Family 5 cellulase enzyme for use in treating cellulose-containing goods.

BACKGROUND OF THE INVENTION

Cellulase enzymes are widely used to improve the appearance and softness of cellulose-containing fabrics. One common application of cellulase enzymes is for treating denim fabrics so as to impart to them a "stone-washed" appearance. Such a process is known in the industry as "bio-stoning". Cellulase enzymes have largely replaced stones for generating the soft, faded denim that is desired by consumers. A second widespread application of cellulase enzymes is to remove cotton fuzz and loose surface fibers in or on the fabric. This process, known as "depilling" or "biopolishing", smooths the surface of the fabric, which in turn improves its softness and appearance. Cellulase treatment also aids in the prevention of subsequent formation of fiber pills that make the garments appear worn.

Fungi such as *Trichoderma* secrete a number of different cellulase enzymes (also referred to herein as an "enzyme mixture") that are individually known as components. The more prevalent of these enzyme components include cellobiohydrolase (CBH), endoglucanase (EG), and beta-glucosidase enzymes. Cellulase enzyme components typically comprise a cellulose binding domain (CBD) and a catalytic domain. A region between these two domains known as a "linker" serves as a flexible spacer between the CBD and the catalytic domain.

The cellobiohydrolase (CBH) and endoglucanase (EG) components can be further divided into glycosyl hydrolase families (Davies and Henrissat, 1995), some of which have been identified as contributing to improvements in the look and feel of the fabric. *Trichoderma reesei* is a widely studied and industrially important fungus for the production of cellulases. It produces at least six genetically different cellulases: two cellobiohydrolases (Cel7A and Cel6A, formerly known as CBH I and II, respectively) and at least four endo-glucanases (Cel7B, Cel5A, Cel12A and Cel45A, formerly known as EGI, EGII, EGIII and EGV, respectively).

Efforts have been made to improve the properties of cellulase mixtures for textile applications by varying the relative proportions of the cellobiohydrolase and endoglucanase components in a secreted enzyme mixture relative to the natural mixture. For instance, WO 92/17574 discloses an approach that involves adjusting the amounts of EG type components relative to CBH I type components (Cel7A) so that the protein weight ratio is greater than 5:1. Cotton-containing fabrics treated with such compositions exhibited decreased strength loss during textile treatment compared to fabrics containing greater amounts of CBHI type (Cel7A) components.

Improvements in depilling and bio-stoning have also been achieved by elevating the content of single components in the enzyme mixture. U.S. Pat. No. 5,858,767 discloses *Trichoderma* cellulase preparations enriched in the CBHII cellobiohydrolase (Cel6A) in an otherwise normal background cellulase composition. Such compositions were found to improve the appearance of fabrics in depilling applications. U.S. Pat. No. 5,874,293 discloses cellulase mixtures enriched in EGII endoglucanase (Cel5A) that show improvements in bio-stoning applications. EP 866 165 discloses enzyme compositions enriched in EGII (Cel5A) with improvements in depilling applications.

However, despite these efforts, there is a continuous need for improved cellulases and compositions thereof that are more efficient in fabric treatment and in other fields where cellulases have been traditionally used. In particular, there is a continuous need for more catalytically efficient cellulases to improve process economics. Such a need could be met by improving the specific activity of components in the enzyme mixture. By providing for a more active cellulase, less enzyme may be required, which in turn could significantly reduce processing costs.

Researchers have modified Family 5 cellulases (also referred to herein as "Cel5") by protein engineering with the aim of improving their activity for the efficient conversion of cellulose to glucose during the production of ethanol from biomass. In *Acidothermus cellulolyticus* Cel5A (SEQ ID NO:13; AcCel5A), a Y245G mutation increased the activity of the enzyme on dilute-acid pretreated yellow poplar sawdust (Baker et al., 2005). Increased activity was mainly driven by a decrease in inhibition by cellobiose.

Variants of *Bacillus subtilis* (strain BME-15) Cel5A (SEQ ID NO:14; BsCel5A) carrying multiple catalytic domains and CBD mutations exhibited increased specific activity of up to 2.68 fold using carboxymethyl cellulose (CMC) as a substrate (Lin et al., 2008). However, the activity level reached by the best mutant was 4.88 U/mg, whereas *Trichoderma* EGII activity on the same substrate was reported to be 39.9 U/mg (Xiao et al., 2002).

In addition, the effect of genetic modification on the activity of *Trichoderma reesei* Cel5A (TrCel5A; SEQ ID NO:1) at pH values higher than its optimal range has been examined. Commercially available endoglucanases from *Trichoderma reesei* have optimum activity in the pH range of 4-6. The goal of such studies is to increase the activity of the enzyme at higher pH values so that it can be utilized in industrial processes that operate at neutral or alkaline conditions.

Mutation N321T in the mature TrCel5A cellulase (without the secretion signal) was identified to increase the optimal pH of the enzyme by 0.6 to 0.8 pH units over the wild-type enzyme via directed evolution (Wang et al., 2005). Site-saturation of this position showed that an N to R substitution resulted in the highest shift in optimum pH with an increase of 1.4 pH units (Qin et al., 2008a). However, the specific activity of this variant was greatly decreased compared to wild-type. After subsequent error-prone PCR and DNA shuffling steps, a variant Q139R/L218H/W276R/N342T (equivalent to Q118R/L197H/W255R/N321T in SEQ ID:1) was isolated with an optimal pH increase of 1.4 units without significant loss in specific activity (Qin et al., 2008b).

Studies on a Family 5 alkalophilic cellulase NK1 from *Bacillus cellulosilyticus* (SEQ ID NO:15; BcNK1) (formerly known as *Bacillus* sp. N-4) showed that the C-terminal portion of the catalytic domain is critical for the alkalophilicity of enzyme, especially residues S287 and A296 (Nakamura et al., 1991; Park et al., 1993). Mutating these residues for the equivalent residues in *Bacillus subtilis* neutral cellulase (BSC) made the *Bacillus cellulosilyticus* NK1 pH profile very similar to the *Bacillus subtilis* pH profile. Among these two mutations, S287N caused a greater effect on the pH profile than A296S.

SUMMARY OF THE INVENTION

It is an object of the present invention to provide a modified Family 5 cellulase.

The present invention relates to a modified Family 5 cellulase and an enzyme mixture comprising same. The present invention also relates to a genetic construct comprising nucleic acid sequences encoding the modified Family 5 cellulase, methods for the production of the modified Family 5 cellulase from host strains and the use of the modified Family 5 cellulase in textile treatment, including, but not limited to depilling and bio-stoning.

The present invention provides a modified Family 5 cellulase comprising a substitution of an amino acid at position 363 with an alanine, a serine or a threonine. Generally, the substituted amino acid at position 363 is non-native. For example, this means that the parental or wild-type cellulase from which the modified Family 5 cellulase is derived does not have an alanine, serine or threonine at position 363. The position of the amino acid substitution is determined from alignment of the modified Family 5 cellulase with a *Trichoderma reesei* Cel5A amino acid sequence as set forth in SEQ ID NO:1, as described hereinafter. The present invention also relates to an enzyme mixture comprising the modified Family 5 cellulase as defined above.

The modified Family 5 cellulase and enzyme mixtures comprising same may be used to treat cellulose-containing goods. In one embodiment, the invention provides a process for bio-stoning that comprises a step of contacting the denim fabric or denim garments with the enzyme mixture or the modified Family 5 cellulase. Furthermore, the present invention relates to a process for depilling that comprises a step of contacting the cellulose-containing goods with the modified Family 5 cellulase. In one example of the invention, in the step of contacting, the cellulose-containing goods are fabrics or garments.

The present invention also provides a detergent composition comprising the modified Family 5 cellulase.

Moreover, the present invention provides a genetic construct comprising a nucleic acid sequence encoding the modified Family 5 cellulase. Also provided is a genetically modified microbe that comprises the genetic construct. The invention also relates to a process for producing the modified Family 5 cellulase, comprising the steps of growing the genetically modified microbe in a culture medium under conditions that induce the expression and secretion of the modified Family 5 cellulase and recovering an enzyme mixture comprising the modified Family 5 cellulase from the culture medium.

The present invention also provides an enzyme mixture comprising a modified *Trichoderma reesei* Cel5A enzyme that has at least a substitution of a glycine to an alanine at position 363. Further provided is an enzyme mixture comprising a *Trichoderma reesei* Cel5A enzyme having a G363A, S or T amino acid substitution as set forth in SEQ ID NO:17, SEQ ID NO:18 or SEQ ID NO:19, respectively.

The present invention also relates to a modified Family 5 cellulase comprising a substitution of an amino acid at position 363 with an alanine, a serine or a threonine and that exhibits an increase in specific activity of at least 1.2 fold relative to a parental Family 5 cellulase or a corresponding wild-type Family 5 cellulase.

In features of any of the foregoing embodiments of the invention, the modified Family 5 cellulase is derived from a fungal Family 5 cellulase enzyme. In a further feature of any of the foregoing embodiments of the invention, the substituted amino acid at position 363 is an alanine. In yet a further feature of any of the foregoing embodiments of the invention, the alanine at position 363 is non-native.

Modified Family 5 cellulases of the invention exhibit improvements in specific activity relative to the parental or wild-type enzyme. Family 5 cellulases exhibiting such improvements in specific activity have potential value in industries for the treatment of cellulose-containing goods such as depilling or bio-stoning, or for the production of fermentable sugar in the production of biofuel, biogas or other chemicals.

DETAILED DESCRIPTION OF THE INVENTION

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Modified Family 5 Cellulases

The amino acid sequences for numerous naturally occurring Family 5 cellulases of fungal and bacterial origin have been elucidated (Wang et al., 1993). Regions of Family 5 cellulases are well conserved in most Family 5 cellulase enzymes and this has allowed the alignment of parts of the catalytic domains of family members (Wang et al., supra).

Figure 1:
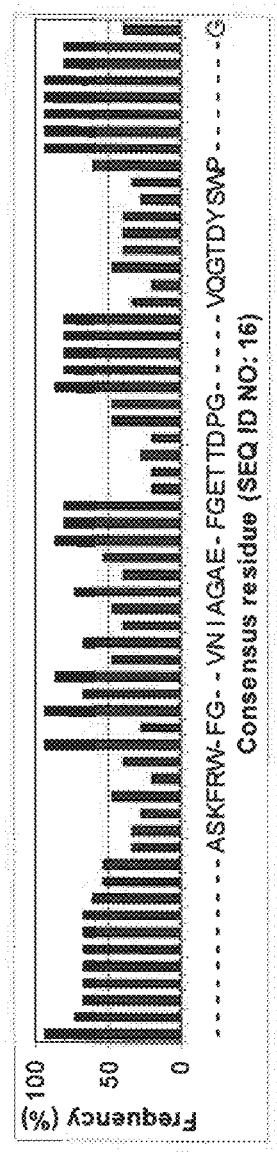
FIG. 1 shows an amino acid sequence alignment among fifteen selected cellulases from Glycosyl Hydrolase (GH) Family 5, the percent sequence identity of each amino acid sequence to amino acids 71 to 397 of TrCel5A (SEQ ID NO:1) and a graphical representation of the frequency of occurrence of the consensus amino acid at each position of the alignment among the fifteen selected Family 5 cellulases. For cellulases with a cellulose-binding domain, only the catalytic core sequences are presented. The catalytic residues at the equivalent position 218 and 329 in TrCel5A are indicated with an arrow. The conserved residues at the equivalent position 130, 174, 217, 288, and 290 in TrCel5A are indicated with an asterisk.
Figure 1:
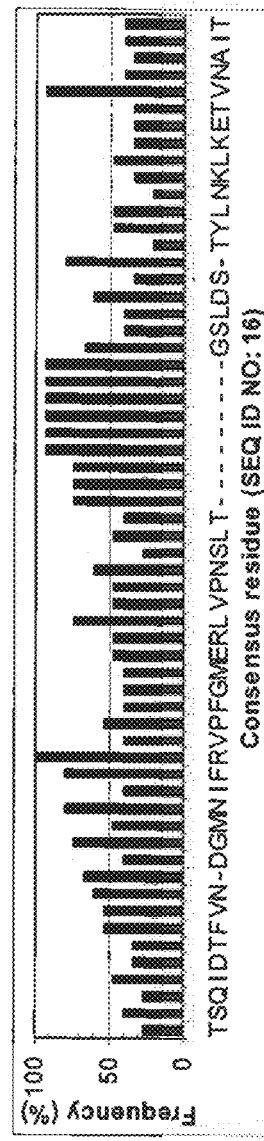
Figure 1:
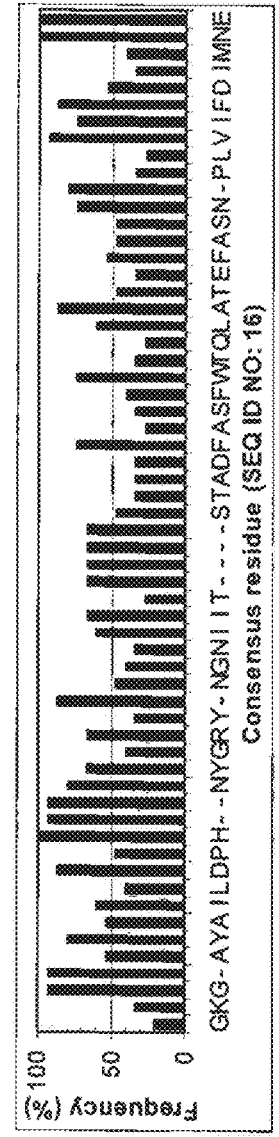
Figure 1:
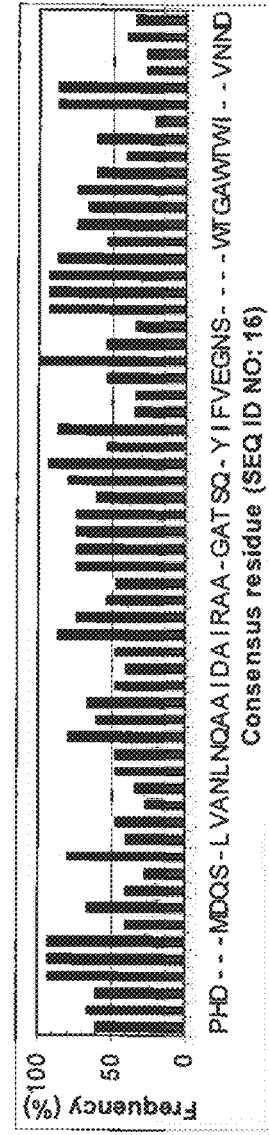
Figure 1:
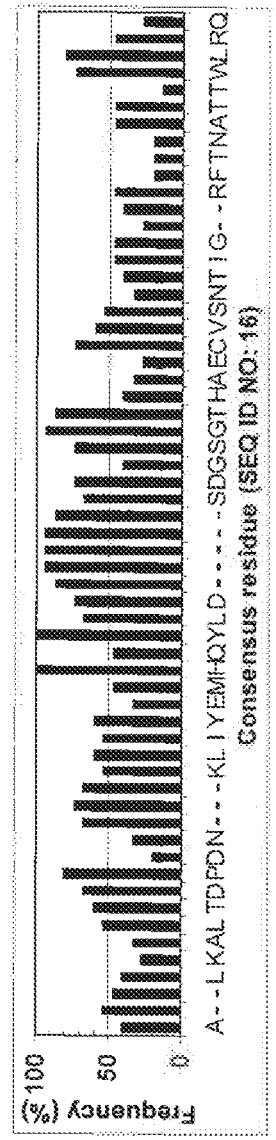
Figure 1:
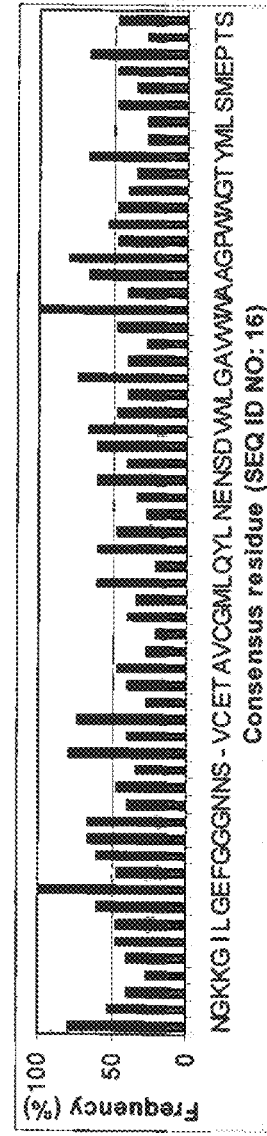
Figure 1:
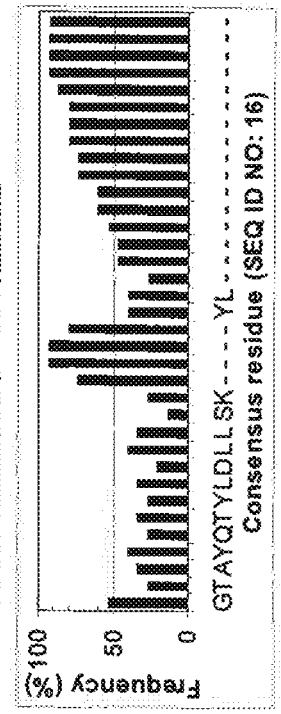

Table 1 below includes a representative list of fifteen known Family 5 cellulases and FIG. 1 shows an amino acid sequence alignment among the cellulases provided in the table.

TABLE 1

Examples of known Family 5 cellulases

| SEQ ID NO: | Abbreviated name | Organism |
| --- | --- | --- |
| 1 | TrCel5A | *Trichoderma reesei* |
| 2 | PjEgl2 | *Penicillium janthinellum* |
| 3 | MpEgl2 | *Macrophomina phaseolina* |
| 4 | CfEgl1 | *Cryptococcus flavus* |
| 5 | AnEglA | *Aspergillus nidulans* |
| 6 | AkCel5A | *Aspergillus kawachii* |
| 7 | MpEgl1 | *Macrophomina phaseolina* |
| 8 | VvEG1 | *Volvariella volvacea* |
| 9 | TaEg1 | *Thermoascus aurantiacus* |
| 10 | AaCel1 | *Aspergillus aculeatus* |
| 11 | HiCMC3 | *Humicola insolens* |
| 12 | OjCelB29 | *Orpinomyces joyonii* |
| 13 | AcCel5A | *Acidothermus cellulolyticus* |
| 14 | BsCel5A | *Bacillus subtilis* |
| 15 | BcNK1 | *Bacillus cellulosilyticus* |

As used herein, the term "TrCel5A numbering" means that the amino acid position in an amino acid sequence is determined by alignment with a wild-type *Trichoderma*, also referred to herein as "TrCel5A", the amino acid sequence of which is provided in SEQ ID NO:1. The amino acid numbering is based on the sequence of the mature, secreted protein. By aligning the amino acids to optimize the sequence similarity between the Family 5 catalytic domains of cellulase enzymes, and by using the amino acid numbering of TrCel5A as the basis for numbering, the positions of amino acids within other Family 5 cellulases can be determined relative to TrCel5A.

With reference to FIG. 1, there is a particularly high degree of conservation of certain amino acid residues among Family 5 cellulases. As shown in the figure, multiple alignment across these fifteen Family 5 cellulase amino acid sequences (Table 1) reveals that most naturally occurring Family 5 cellulases have conserved R130, H174, E217, E218, H288, Y290 and E329 residues, as determined by "TrCel5A numbering" (See also Wang et al., 1993).

As used herein, the term "Family 5 cellulase" or "Cel5" encompasses a carbohydrate active cellulase enzyme that contains a glycohydrolase (GH) Family 5 catalytic domain that is classified under EC 3.2.1.4. The term also includes any carbohydrate active enzyme that exhibits at least hydrolysis of (1→4)-β-D-glucosidic linkages, including those enzymes with the conserved R130, H174, N217, E218, H288, Y290 and E329 residues (determined by TrCel5A numbering described above).

Enzymes of Family 5 share a common (beta/alpha) 8-barrel fold and a catalytic mechanism resulting in a net retention of the anomeric sugar conformation. Glycosyl hydrolase catalysis is driven by two carboxylic acids found on the side chain of aspartate and/or glutamate residues (Ly and Withers, 1999). In enzymes using a retaining mechanism, one residue, initially deprotonated, acts as a nucleophile attacking the glycosidic bond in the first step. This forms a glycosyl-enzyme specie which is broken down in a second step. The other catalytic residue serves as an acid/base catalyst that donates a proton to the departing free sugar. In the second step, this residue deprotonates a water molecule, which then breaks the covalent bond in the substrate-enzyme complex to complete the hydrolysis process. The product is then released and the catalytic residues are back to their original protonation state. In Family 5 enzymes, both catalytic residues are glutamates (URL cazy.org/) (Cantarel et al., 2008). In TrCel5A, residue E329 and E218 are the nucleophile and the acid/base respectively (Macarron et al., 1993). As mentioned previously, these two residues are highly conserved among family members (Wang et al., 1993).

Many Family 5 cellulases, including the *Trichoderma* Cel5A enzyme (TrCel5A), comprise three domains (Stahlberg et al., 1988). In the case of *Trichoderma*, the N-terminal region (SEQ ID NO:1 residues 1 to 36) is a cellulose binding domain (CBD) belonging to CBM (carbohydrate-binding module) Family 1 (URL cazy.org/) (Cantarel et al., 2008). The C-terminal domain (SEQ ID NO:1 residues 71 to 397) is the glycohydrolase (GH) Family 5 catalytic domain which is responsible for the catalytic activity. The region between these two domains (SEQ ID NO:1 residues 37 to 70) is a linker rich in proline and hydroxy-amino acids (serine and threonine) that serves as a flexible spacer between the CBD and the catalytic domain.

By "modified Family 5 cellulase", it is meant a Family 5 cellulase that contains one or more genetic alteration introduced by molecular biology techniques. Such techniques include, but are not limited to, site-directed mutagenesis, cassette mutagenesis, random mutagenesis, including that conducted on isolated DNA or by exposing a microorganism to a mutagen, such as UV light, synthetic oligonucleotide construction, cloning, sub-cloning, amplification by PCR, in vitro synthesis and other genetic engineering techniques (Eijsink et al., 2005). It will be understood that the modified Family 5 cellulase may be derived from any suitable Family 5 cellulase. That is, it may be derived from a naturally-occurring or "wild-type" Family 5 cellulase or from a Family 5 cellulase that already contains other amino acid substitutions, deletions or insertions. For example, the Family 5 cellulase may be derived from a parental Family 5 cellulase, as defined hereinafter.

By the term "isolated", it is meant a Family 5 cellulase that exists in an environment that is different from the environment in which it exists in nature or that is different from a naturally-occurring composition. For example, the isolated Family 5 cellulase may be one of a consortium of cellulase enzymes secreted by a microbe, such as in a fermentation process described below. Following fermentation, the fermentation broth containing the modified Family 5 cellulase may be used directly, or the modified Family 5 cellulase may be separated from the fungal cells, for example by filtration or centrifugation.

By the term "wild-type Family 5 cellulase" it is meant a Family 5 cellulase that does not contain any genetic alteration(s) introduced by molecular biology techniques, such as those described above.

By the term "parental Family 5 cellulase", it is meant a Family 5 enzyme that is identical to the modified Family 5 cellulase of the invention, except that it does not contain the amino acid substitution(s) introduced in accordance with the invention. For example, the parental Family 5 cellulase may not contain a G363X, wherein X is alanine, serine or threonine. The parental Family 5 cellulase and the modified Family 5 of the invention may contain other amino acid modifications in their sequences relative to a wild-type enzyme, provided that the sequences are identical except for the amino acid substitution of the invention.

By the term "corresponding wild-type Family 5 cellulase", it is meant a wild-type Family 5 cellulase from which the modified Family 5 cellulase of the invention is derived.

The modified Family 5 cellulase of the invention comprises at least a mutation at position 363 to an alanine, serine or threonine residue. Generally, the amino acid introduced at position 363 is "non-native", meaning that that it does not naturally occur at the corresponding position in the wild-type Family 5 cellulase sequence from which it is derived. The position of the 363 mutation is determined by alignment with a wild-type *Trichoderma reesei* Family 5 enzyme, referred to herein as TrCel5A numbering.

Sequence identity can be readily determined by alignment of the amino acids of the two sequences, either using manual alignment, or any sequence alignment algorithm as known to one of skill in the art, for example but not limited to, BLAST algorithm (BLAST and BLAST 2.0; Altschul et al., 1997; and Altschul et al., 1990), the algorithm disclosed by Smith and Waterman, 1981, by the homology alignment algorithm of Needleman and Wunsch, 1970, by the search for similarity method of Pearson and Lipman, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)). In the case of conducting BLAST alignments and sequence identity determinations for cellulase enzymes, only the amino acid sequences comprising the catalytic domains are considered.

Additional mutations may be introduced into the modified Family 5 cellulase, provided that such mutations do not significantly compromise the structure and function of the enzyme. As would be appreciated by those of ordinary skill in the art, but without being limiting in any manner, additional mutations may be introduced in regions of low sequence conservation among Family 5 cellulases. The alignment of the Family 5 cellulases in FIG. 1 includes a bar graph below the sequences showing the occurrence of each consensus amino acid at each position among the selected family members. The sequence information contained in FIG. 1 may be used as guidance by those of ordinary skill in the art when introducing an additional mutation(s) besides that at position 363. For example, amino acid substitutions may be introduced at amino acid positions that have less than 50%, 45%, 40%, 35%, 30%, 25%, 20%, 15%, 10% or 5% conservation relative to the consensus residue (SEQ ID NO:16) as determined by alignment with the set of amino acid sequences provided in FIG. 1.

The modified Family 5 cellulase of the invention may contain amino acid substitutions "consisting essentially of the amino acid substitution at position 363". By this it is meant that the modified Family 5 cellulase contains no more than 20 other amino acid substitutions in its sequence relative to a corresponding wild-type Family 5 cellulase.

In another example of the invention, the modified Family 5 cellulase contains no more than 15 other amino acid substitutions, no more than 10 other amino acid substitutions or no more than 5 other amino acid substitutions in its sequence. As mentioned previously, such additional amino acid substitutions may be introduced at non-conserved positions in the amino acid sequence. In further embodiments, the modified Family 5 cellulase contains 1-20 or 1-10 amino acid substitutions in its sequence relative to a corresponding wild-type Family 5 cellulase.

The additional amino acid substitutions may be introduced by standard molecular biology techniques such as random mutagenesis, site-directed mutagenesis or directed evolution.

Although the CBD is not required for the Family 5 cellulase to be active, its presence can make the enzyme more catalytically efficient (Stahlberg et al., 1988; Ito et al., 2004). The replacement of *T. reesei* Cel7A and Cel6A CBDs for the native TrCel5A CBD increases activity by about 1.7 times compared to the wild-type enzyme (Ito et al., 2004). Similarly, CBD mutants with increased binding to cellulose and activity on carboxymethyl cellulose were found through a combinatorial library targeting two CBD residues (Fukuda et al., 2006). In one example of the invention, the Family 5 cellulase is functionally linked to a cellulose binding domain with a high affinity for crystalline cellulose.

However, modified Family 5 cellulase enzymes of the invention need not contain a CBD. Indeed, it is well known that cellulases utilized in depilling applications can be "cored", meaning that the enzyme does not contain the CBD or both the linker and the CBD. U.S. Pat. Nos. 5,700,686 and 5,916,799 (which are incorporated herein by reference) describe methods for removing cellulose binding domains by protease treatment, although cellulases that lack a CBD can also be produced by genetic modification.

Representative examples of Family 5 cellulases that do not contain an alanine at position 363 of the wild-type sequence (TrCel5A numbering) and that can be modified in accordance with the invention include enzyme species from the genera of *Trichoderma, Hypocrea, Penicillium, Botryotinia, Macrophomina, Aspergillus, Orpinomyces, Acidothermus, Pestalotiopsis, Myceliophthora, Chrysosporium* and *Xylella*. In one example of the invention, the modified Family 5 cellulase is derived from species selected from the group consisting of *Trichoderma reesei* (SEQ ID NO:1), *Trichoderma viride, Hypocrea jecorina, Penicillium decumbens, Penicillium janthinellum* (SEQ ID NO:2), *Botryotinia fuckeliana, Xylella fastidiosa, Macrophomina phaseolina* (MpEgl2, SEQ ID NO:3), *Aspergillus kawachii* (SEQ ID NO:6), *Aspergillus aculeatus* (SEQ ID NO:10), *Orpinomyces joyonii* (SEQ ID NO:12) and *Acidothermus cellulolyticus* (SEQ ID NO:13). The sequences of each of these Family 5 cellulases are publicly available. That is, they can be readily obtained by those of ordinary skill in the art from public databases.

Modified Family 5 cellulases of the invention may have conserved R130, H174, N217, E218, H288, Y290 and E329 residues (determined by TrCel5A numbering) and exhibit greater than about 20%, 30%, 40%, 50%, 60%, 70%, 80% or 90% sequence identity with the TrCel5A catalytic domain (amino acids 71-397 of SEQ ID NO:1).

In another embodiment of the invention, the modified Family 5 cellulase has greater than about 40%, 50%, 60%, 70%, 80% or 90% sequence identity with the TrCel5A catalytic domain (amino acids 71-397 of SEQ ID NO:1).

Measurement of the Specific Activity of Modified Family 5 Cellulases

The modified Family 5 cellulase enzyme of the invention exhibits improvements in specific activity. The improvement in specific activity may be measured relative to a parental Family 5 cellulase or relative to a corresponding wild-type Family 5 cellulase, as defined above.

The increase in specific activity of the modified Family 5 of the invention can be determined by measuring the degradation of cellulose or other suitable cellulase substrate. There are several known assays that can be used for measuring cellulase activity of the modified and parental Family 5 cellulases. It should be understood, however, that the practice of the present invention is not limited by the method used to assess the activity of the modified Family 5 cellulase.

For example, Family 5 activity can be monitored by measuring the enzyme-dependent creation of reducing sugars, which are quantified in subsequent chemical or chemi-enzymatic assays known to one of skill in the art. Hydrolysis of polysaccharides can also be monitored by chromatographic methods that separate and quantify soluble mono-, di- and oligo-saccharides released by the enzyme. A further method that can be utilized involves determining the change in viscosity with time as the enzyme acts on the substrate. In addition, soluble colorimetric substrates may be incorporated into agar-medium on which a host microbe expressing and secreting a parental or modified Family 5 cellulase enzyme is grown. In such an agar-plate assay, activity of the cellulase is detected as a coloured or colourless halo around the individual microbial colony expressing and secreting an active cellulase.

Examples 10 and 11 provide non-limiting examples of assays that can be employed to determine the activity of the modified Family 5 enzyme relative to a parental or wild-type Family 5 cellulase. For example, the activity of the modified Family 5 cellulase relative to a reference Family 5 cellulase enzyme can be quantified by measuring the reducing ends released from cellulose as measured by glucose equivalents (Example 10). Such an approach generally involves treating a polysaccharide with an enzyme that cleaves glycosidic bonds between its subunits. The anomeric carbon liberated from this bond is termed a reducing end in that it can act as an agent to reduce an assay reagent to produce a measurable signal. Glucose can be used to generate a standard curve for such a reaction as each glucose molecule will have one anomeric carbon and thus one reducing end; the number of molecules and the number of reducing ends are therefore the same for glucose. Example 11 provides a viscometric assay to quantify Family 5 cellulase activity. As set forth therein, enzyme is added to a cellulose substrate, in this case a derivative of cellulose, and the viscosity in centipoise is recorded over the time course of the assay. Endoglucanases such as Cel5 can hydrolyse glycosidic bonds throughout cellulose chains, not just the end, so their action can rapidly reduce the average length of a sample of cellulose chains. The reduction in molecular weight of the cellulose chains results in a decrease in the viscosity of the solution.

The specific activity of the modified Family 5 cellulase enzyme is determined by measuring the activity of the enzyme, typically in units of amount of glucose released per unit of time divided by the weight of the enzyme. For example, the specific activity may be determined in units of micromoles of glucose produced per minute per milligram of enzyme.

Improvements in the activity of the modified Family 5 cellulase relative to a parental or a wild-type Family 5 cellulase may be between about 1.2 fold and about 10 fold, between about 1.2 fold and about 5 fold, or between about 1.2 fold and about 4 fold, or between about 1.2 fold and about 3 fold or between about 1.2 fold and about 2 fold or between about 1.2 fold and about 1.9 fold or between about 1.2 fold and about 1.8 fold or between about 1.2 fold and about 1.7 fold or between about 1.2 fold and about 1.5 fold.

The improvement in activity of the modified Family 5 cellulase relative to the reference Family 5 cellulase (wild-type or parental) is determined by comparing the activities under identical reaction conditions as would be appreciated by those of ordinary skill in the art.

Measuring Increases in pH Optimum

The modified Family 5 cellulase of the invention may exhibit an increase in its pH optimum relative to a corresponding wild-type or parental enzyme. The pH optimum of the modified Family 5 cellulase may be increased by known techniques, including but not limited to random mutagenesis, site-directed mutagenesis or directed evolution. The pH optimum of modified Family 5 cellulases produced by such known methods may be determined using known methodologies including those set forth below.

As discussed previously, glycosyl hydrolase catalysis by Family 5 cellulases is driven by two carboxylic acids found on the side chain of the two glutamate residues (Ly and Withers, 1999). These amino acids possess two pKa's: $pK_{a1}$ and $pK_{a2}$ for the carboxylic acid and the amine respectively. Shifts in the pH optimum of the modified Family 5 cellulase of the invention relative to a parental or wild-type Family 5 cellulase can be measured by determination of the $pK_{a1}$ and/or $pK_{a2}$ of the glutamate residues in the active site using techniques known to those of ordinary skill in the art.

Increases in the pH optimum of a Family 5 cellulase may also be determined by measuring the maximum effective pH of the enzyme relative to a reference Family 5 cellulase, such as a wild-type or parental Family 5 cellulase. The maximum effective pH is the highest pH at which a cellulase exhibits at least 80% of its optimal activity. The pH range for which at least 80% of the optimal (maximum) activity is determined and the highest pH is the maximum effective pH.

Genetic Constructs Encoding Modified Family 5 Cellulase

The present invention also relates to genetic constructs comprising a nucleic acid sequence encoding a modified Family 5 cellulase. The modified cellulase-encoding nucleic acid sequence may be operably linked to regulatory nucleic acid sequences directing the expression and secretion of the modified Family 5 cellulase from a host microbe. By "regulatory nucleic acid sequences" it is meant a promoter and a nucleic acid sequence encoding a secretion signal peptide. In an embodiment of the invention, the regulatory nucleic acid sequences are derived from genes that are highly expressed and secreted in the host microbe under industrial fermentation conditions. Without being limiting, the regulatory sequences may be derived from one or more of the *Trichoderma reesei* cellulase or hemicellulase genes.

The genetic construct may further comprise a selectable marker gene to enable isolation of a genetically modified microbe transformed with the construct as is commonly known to those of skill in the art. The selectable marker gene typically confers resistance to (i) an antibiotic, or (ii) the ability to grow on medium lacking a specific nutrient to the host organism that otherwise could not grow under the selective conditions. However, the present invention is not limited by the choice of a particular selectable marker gene, and one of skill in the art may readily determine an appropriate marker gene. In one embodiment of the invention, the selectable marker gene confers resistance to hygromycin, phleomycin, kanamycin, geneticin, or G418, complements a deficiency of the host microbe in one of the trp, arg, leu, pyr, ura, his, or ade genes or confers the ability to grow on acetamide as a sole nitrogen source.

As would be appreciated by those of skill in the art, the genetic construct may further comprise other nucleic acid sequences, for example, transcriptional terminators, nucleic acid sequences encoding peptide tags, synthetic sequences to link the various nucleic acid sequences together, origins of replication, and the like.

Genetically Modified Microbes Producing Modified Family 5 Cellulases

The modified Family 5 cellulase is expressed and secreted from a genetically modified microbe comprising a genetic construct encoding the modified Family 5 cellulase. The modified Family 5 cellulase may be part of an enzyme mixture containing other cellulase enzymes secreted by the host microbe.

By the term "enzyme mixture", it is meant any mixture comprising enzymes in addition to modified Family 5 cellulase. For example, the enzyme mixture may comprise cellulase enzymes secreted from a host microbe, including, but not limited to a fungal host strain.

The host microbe may be any suitable yeast or a filamentous fungus, such as those microbes that are members of the phylum Ascomycota. Genera of yeasts useful as host microbes for the expression of modified Family 5 cellulases of the present invention include *Saccharomyces* spp, *Pichia* spp, *Hansenula* spp, *Kluyveromyces* spp, *Yarrowia* spp, and *Arxula* spp. Genera of fungi useful as microbes for the expression of modified Family 5 cellulases of the present invention include *Trichoderma* spp, *Hypocrea* spp, *Aspergillus* spp, *Fusarium* spp, *Humicola* spp, *Neurospora* spp, and *Penicillium* spp. In a most preferred embodiment, the host microbe is an industrial strain of *Trichoderma reesei*.

The genetic construct may be introduced into the host microbe by a number of methods known by those of ordinary skill in the art, including but not limited to, treatment of cells with CaCl2, electroporation, biolistic bombardment and PEG-mediated transformation of protoplasts (e.g. White et al., WO 2005/093072).

According to one embodiment of the invention, the modified Family 5 cellulase of the invention is overexpressed from the host microbe. Overexpression can be achieved by introducing into a host microbe a genetic construct containing the gene encoding the modified Family 5 cellulase. The mature Family 5 cellulase may be operably linked to regulatory sequences driving protein expression and secretion, including: i) a sequence encoding a secretion signal peptide from either a native, homologous or heterologous secreted protein; and ii) a constitutive or regulated promoter derived from a gene which is highly expressed in the host microbe under industrial fermentation conditions. In addition, a translational enhancer may be added to increase protein translation. Moreover, multiple copies of the genetic construct containing the gene encoding the modified Family 5 cellulase may be introduced into the microbe, thereby increasing expression levels.

The genetic construct may contain sequences that allow it to recombine with sequences in the genome of the host microbe so that it integrates into the host genome. The genetic construct may also integrate without any specific sequences with which it can recombine. For example, the construct can integrate by random insertion through non-homologous end joining and recombination. Alternatively, the construct may remain in the host in non-integrated form, in which case it replicates independently from the host microbe's genome.

The construct may integrate at any suitable locus within the host microbe's genome. In one embodiment of the invention, the host microbe possesses a disrupted cel5 gene and the genetic construct is inserted into a locus different from that of the wild-type cel5 gene. Since the microbe is deficient in the production of the corresponding wild-type Family 5 cellulase, only the modified Family 5 cellulase will be secreted by the microbe. Non-limiting examples of such microbe strains are the P976 transformants of FIGS. 4-6. These microbial strains are advantageous in that the activity of the modified Family 5 cellulase secreted from the microbe is not diluted by the less active wild-type Family 5 cellulase. However, it should be appreciated that the invention also includes expression of the modified Family 5 cellulase from a host microbe that also expresses one or more wild-type Family 5 cellulase gene(s). (See, for example, the P998 strains of FIGS. 4-6 which express TrCel5A from the endogenous wild-type gene as well as the modified TrCel5A). Alternatively, the genetic construct is inserted into the microbe's genome at the endogenous Family 5 cellulase locus so as to replace the wild-type gene.

It should be appreciated that the invention also encompasses changing the expression levels of the other cellulase components relative to corresponding unmodified host (parental host). That is, the enzyme mixture comprising the modified Family 5 cellulase of the invention may be obtained from a host strain that has been genetically modified so as to overexpress, underexpress or not express one or more of the other cellulase components. In addition to the overexpression techniques set forth above, the expression levels of the other cellulase components may be increased by the introduction of extra copies of corresponding cellulase component or by the introduction of a promoter upstream of the native gene that increases the level of expression of the native gene over endogenous levels. Changes in expression can also be achieved by mutagenesis and selection of strains with desired expression levels. Underexpression may be achieved by the production of strains deficient in the production of a specific cellulase component(s), using techniques know to those of ordinary skill in the art.

Moreover, expression levels can be modulated by adjusting the fermentation conditions, such as by changing the composition of the feed, or by altering the pH or temperature of the fermentation. Yet another means for adjusting expression levels of cellulase involves the modification of cellulase secretion pathways or modification of cellulase transcriptional and/or translational regulation systems and/or post-translational protein maturation machinery (e.g. transcription factors, protein chaperones).

After selecting the recombinant host strains expressing the modified Family 5 cellulase, they may be cultured in submerged liquid fermentations under conditions that induce the expression of the modified Family 5 cellulase. According to one example of the invention, the modified Family 5 cellulase is secreted by a genetically modified microbe grown in submerged liquid culture fermentation and separated from the cells at the end of the fermentation. The cells may be separated by filtration, centrifugation, or other processes familiar to those skilled in the art. The cell-free modified Family 5 cellulase-containing fraction may then be concentrated (for example, via ultrafiltration), preserved, and/or stabilized prior to use.

Production of Modified Family 5 Cellulases

The modified Family 5 cellulase of the present invention may be produced in a fermentation process using a genetically modified microbe comprising a genetic construct encoding the modified Family 5 cellulase, e.g., in submerged liquid culture fermentation.

Submerged liquid fermentations of microorganisms, such as *Trichoderma* and related filamentous fungi, are typically conducted as a batch, fed-batch or continuous process. In a batch process, all the necessary materials, with the exception of oxygen for aerobic processes, are placed in a reactor at the start of the operation and the fermentation is allowed to proceed until completion, at which point the product is harvested. A batch process for producing the modified Family 5 cellulase of the present invention may be carried out in a shake-flask or a bioreactor.

In a fed-batch process, the culture is fed continuously or sequentially with one or more media components without the removal of the culture fluid. In a continuous process, fresh medium is supplied and culture fluid is removed continuously at volumetrically equal rates to maintain the culture at a steady growth rate.

Fermentation medium comprises a carbon source, a nitrogen source and other nutrients, vitamins and minerals which can be added to the fermentation media to improve growth and enzyme production of the genetically modified microbe. These other media components may be added prior to, simultaneously with or after inoculation of the medium with the genetically modified microbe.

When producing the modified Family 5 cellulase of the present invention, the carbon source may comprise a carbohydrate that will induce the expression of the modified Family 5 cellulase from a genetic construct in the genetically modified microbe. For example, if the genetically modified microbe is a strain of *Trichoderma*, the carbon source may comprise one or more of cellulose, cellobiose, sophorose, and related oligo- or poly-saccharides known to induce expression of cellulases and beta-glucosidase in *Trichoderma*.

In the case of batch fermentation, the carbon source may be added to the fermentation medium prior to or simultaneously with inoculation. In the cases of fed-batch or continuous operations, the carbon source may also be supplied continuously or intermittently during the fermentation process. For example, when the genetically modified microbe is a strain of *Trichoderma*, the carbon feed rate is between 0.2 and 4.0 g carbon/L of culture/h, or any amount therebetween.

The process for producing the modified Family 5 cellulase of the present invention may be carried at a temperature from about 20° C. to about 50° C., or any temperature therebetween, for example from about 25° C. to about 37° C., or any temperature therebetween, or from 20, 22, 25, 26, 27, 28, 29, 30, 32, 35, 37, 40, 45 or 50° C. or any temperature therebetween.

The process for producing the modified Family 5 cellulase of the present invention may be carried out at a pH from about 3.0 to 6.5, or any pH therebetween, for example from about pH 3.5 to pH 5.5, or any pH therebetween, for example from about pH 3.0, 3.2, 3.4, 3.5, 3.7, 3.8, 4.0, 4.1, 4.2, 4.3, 4.4, 4.5, 4.6, 4.7, 4.8, 4.9, 5.0, 5.2, 5.4, 5.5, 5.7, 5.8, 6.0, 6.2, 6.5 or any pH therebetween.

Following fermentation, the fermentation broth containing the modified Family 5 cellulase may be used directly, or the modified Family 5 cellulase may be separated from the fungal cells, for example by filtration or centrifugation. Low molecular solutes such as unconsumed components of the fermentation medium may be removed by ultra-filtration. The modified Family 5 cellulase may be concentrated, for example, by evaporation, precipitation, sedimentation or filtration. Chemicals such as glycerol, sucrose, sorbitol and the like may be added to stabilize the cellulase enzyme. Other chemicals, such as sodium benzoate or potassium sorbate, may be added to the cellulase enzyme to prevent growth of microbial contamination.

The modified Family 5 cellulase may be purified by affinity based purification technologies. Such technologies are well known in the art and include any suitable method to selectively bind a component of a biological mixture to a solid support based on a highly specific biological interaction such as that between antigen and antibody or enzyme and substrate. Moreover, the purification can comprise fractionation methods including selective precipitation such as ammonium sulfate precipitation, isoelectric precipitation, selective thermal denaturation or any other suitable method that selectively precipitates the cellulase components. In another example, the purification methodology can comprise chromatographic methods including gel filtration, size exclusion, anion exchange, cation exchange, gel electrophoresis, or other chromatic separation methods known in the art for physically separating proteins.

Treatment of Cellulose-Containing Goods Using the Modified Family 5 Cellulase

The modified Family 5 cellulase of the present invention may be used to treat "cellulose-containing goods". Such treatments include "depilling" or "bio-stoning".

The term "cellulose-containing goods" refers to fabrics, either as piece goods or goods sewn into garments or yarn, comprising cotton or non-cotton containing fibres. The cellulose-containing goods may be treated with the modified Family 5 cellulase of the invention either before or after dyeing and with or without a resinous finish. The term encompasses natural cellulosics and manmade cellulosics. Manmade cellulose containing fabrics include regenerated fabrics that are well known in the art such as rayon.

As used herein, the term "depilling" refers to the use of the modified Family 5 cellulase of the present invention in a controlled hydrolysis of cellulosic fibres in order to modify the surface of the cotton goods in a manner that clears the surface structure by reducing fuzzing. Such treatment can prevent pilling, improve fabric handling like softness and smoothness, which can result in clarification of colour and/or improve moisture adsorbability and dyeability.

Depilling treatment may be carried out during the fabric manufacturing process or in subsequent garment laundering. In either case, treatment is typically carried out by adding cotton goods to a rotating horizontal or vertical drum jet dyer, washing machine, or other device. Such treatments typically provide agitation and shear to the fabric, including loose fibrils. In addition to cellulase enzyme and fabric, other components may be added during depilling, including water, buffer, detergents or surfactants. After treatment, the fabric is removed from the machine or device and dried.

When depilling takes place in a typical manufacturing process, the treatment time may be between about 15 to about 120 minutes; treatment temperature may be about 35° C. to about 60° C.; the ratio of liquor to fabric may be between about 2.5:1 and about 10:1 by weight; and the pH may be about 4.0 to about 6.0. When depilling takes place in a typical garment laundering, the treatment time is about 10 to about 60 minutes, the treatment temperature is about 20° C. to about 70° C., the ratio of liquor to fabric is between about 2.5:1 and about 10:1 by weight and the pH is about 4.0 to about 9.5 or about 4.0 to about 6.0.

The amount of cellulase mixture used to depill depends on the concentration of active protein in the cellulase mixture, the amount of cotton goods being treated, the desired degree of depilling, the time of treatment and other parameters well-known to those of ordinary skill in the art. When used for depilling in a typical manufacturing process, an example of a dose of cellulase is between about 0.1 and about 7 g of enzyme protein per kilogram of fabric and more preferably between about 0.5 g and about 4 g of enzyme protein per kilogram of fabric. When used for depilling in a typical garment laundering, the preferred amount of cellulase is generally between about 0.01 g and about 3 g of enzyme protein per kilogram of fabric and more preferably between about 0.05 g and about 2.5 g of enzyme protein per kilogram of fabric.

One non-limiting option for controlling the action of the enzyme is to destroy the enzyme after treatment by heating the solution, adding chemicals to destroy enzyme activity or by drying the cotton goods.

It is contemplated that the modified Family 5 cellulase can be incorporated into detergent compositions. Such detergent compositions may be in any form known in the art. This includes as a liquid diluent, in granules, in emulsions, in gels, or in pastes. When a solid detergent composition is employed, the modified Family 5 cellulase is typically formulated as granules.

"Bio-stoning" of fabric, as used herein, means the use of enzymes in place of, or in addition to, the use of pumice stones for the treatment of fabric or garments, especially denim.

Bio-stoning typically has three steps: desizing, abrasion and after-treatment. Desizing involves removal of starch or other sizing agents usually applied to the warp yarns to prevent damage during the weaving process. Alpha-amylases can be used for such purpose. Abrasion may be performed with the modified Family 5 cellulase enzyme of the invention. Mechanical action is used to remove the dye and the treatment is usually carried out in washing machines, like drum washers. Such treatment produces a "stone-washed" or "worn" look. As a result of uneven dye removal there are contrasts between dyed areas and areas from which dye has been removed.

Abrasion treatments utilizing the modified Family 5 cellulase of the present invention may be carried out either alone or together with pumice stones (when it is desired to achieve a more heavily abraded finish).

Abrasion is generally followed by after-treatment that includes washing and rinsing steps during which detergents, optical brighteners, bleaching agents or softeners may be used. The enzymatic treatment may be stopped by high temperature and/or pH inactivation.

In bio-stoning, neutral to alkaline conditions are sometimes employed for the purpose of achieving a specific level of abrasion or colour to the jean, while minimizing the costs of processing aids such as acidic buffers. In embodiments of the invention, a modified Family 5 cellulase having a pH optimum that is increased relative to a parental Family 5 cellulase is utilized in the bio-stoning process. Examples of pH ranges that can be employed in bio-stoning are 5-8.

Suitable enzyme dosages for imparting a stone-washed appearance to the fabric depend on the desired result, on the treatment method, and on the activity of the enzyme product. Examples of suitable enzyme dosages are about 0.05 to 5 percent, or about 0.5 to 2 percent of the weight of the treated fabric. It should be appreciated that the enzyme dosage greatly depends on the type of fabrics and machinery process conditions.

The temperature of the abrasion reaction can range from about 30° C. to 80° C. and is preferably between about 50° C. and 60° C. The liquor ratio (the ratio of the volume of liquid per weight of fabric) may range from about 3:1 to 20:1, preferably 5:1 to 10:1. The treatment time can range between 15 minutes to 90 minutes and preferably 30 minutes to 60 minutes.

Other Industrial Applications for the Modified Family 5 Cellulase

The modified Family 5 cellulase of the present invention can also be utilized in the production of biofuels or biogas. A cellulase enzyme mixture could be used to convert cellulose to glucose, which is subsequently converted to a biofuel or biogas. The glucose is subsequently fermented to a biofuel such as ethanol or butanol or a biogas such as methane.

Enzyme mixtures containing the modified Family 5 cellulase of the present invention could also be useful for improving the quality of animal feed, whereby plant material is treated with the enzymes prior to or during the feeding.

The present invention will be further illustrated in the following examples. However, it is to be understood that these examples are for illustrative purposes only and should not be used to limit the scope of the present invention in any manner.

EXAMPLES

Example 1 describes the strains and vectors used in subsequent examples. Examples 2 and 3 describe the cloning of the *Trichoderma reesei* Cel5A gene (referred to hereinafter as "trcel5a" or the "trcel5a gene"), transformation of the gene into yeast and the generation of site-saturation mutagenesis libraries of TrCel5A. Examples 4 and 5 relate to the expression of modified TrCel5A from microculture and the high-throughput screening to identify modified Family 5 cellulases with increased specific activity. Examples 6 and 7 describe the cloning and expression in *Trichoderma reesei* of modified Family 5 cellulase with increased specific activity. Example 8 shows the expression and preparation of TrCel5A and modified TrCel5A from large scale culture. Examples 9 and 10 set forth assays for measuring the activity of TrCel5A enzymes. In Example 11, the weight loss of fabric was determined after treatment with TrCel5A and modified TrCel5A cellulases.

Example 1

Strains and Vectors

*Saccharomyces cerevisiae* strain YNL219C BY4742 [11993] (MATα his3Δ1 leu2Δ0 lys2Δ0 ura3Δ0 Δalg9) was obtained from ATCC (cat. No. 4011993). *Escherichia coli* strain DH5α (F-φ80lacZΔM15 Δ(lacZYA-argF)U169 recA1 endA1 hsdR17(rk-, mk+) phoA supE44 thi-1 gyrA96 relA1 λ-) was obtained from Invitrogen (cat. No. 18265-017). The YEp352/PGK91-1ΔNheI-xylss-cbh2 vector is described in co-pending and co-owned, U.S. Publication No. 2008/0076152.

The host *Trichoderma reesei* strain used for the overexpression of TrCel5A-G363A was BTR213aux. This strain was isolated from strain RutC30 (ATCC cat. No. 56765).

RutC30 strain was isolated as a high cellulase producing derivative of the progenitor strain QM6A (Montenecourt et al., 1979). Cellulase hyper-producing strains were generated from RutC30 by random mutation and/or selection. A strain referred to as M2C38 was isolated based on its ability to produce larger clearing zones than RutC30 on minimal media agar containing 1% acid swollen cellulose and 4 g/L 2-deoxyglucose. Next, M2C38 was subjected to further random mutagenesis and the BTR213 strain was isolated by selection on lactose media containing 0.2 μg/mL carbendazim. A uridine auxotroph of BTR213, BTR213aux, was obtained through selection of mutants spontaneously resistant to 0.15% w/v 5-fluoroorotic-acid (FOA).

Example 2

Cloning of the trcel5a Gene into YEp352/PGK91-1ΔNheI-xylss and Transformation in Yeast To isolate *T. reesei* M2C38 genomic DNA, 50 mL of Potato Dextrose Broth (Difco) was inoculated with *T. reesei* M2C38 spores collected from a Potato Dextrose Agar plate with a sterile inoculation loop. The cultures were shaken at 200 rpm for 2-3 days at 28° C. The mycelia was filtered onto a GFA grade glass microfibre filter (Whatman) and washed with cold, deionized water. The fungal cakes were frozen in liquid nitrogen and crushed into a powder with a pre-chilled mortar and pestle. Subsequently, 0.5 g of the powdered biomass was resuspended in 5 mL of 100 mM Tris, 50 mM EDTA, pH 7.5 plus 1% sodium dodecyl sulphate (SDS). The lysate was centrifuged (5000×g for 20 minutes, 4° C.) to pellet cell debris. The supernatant was extracted with 1 volume buffer (10 mM Tris, 1 mM EDTA, pH 8.0) saturated phenol followed by extraction with 1 volume of buffer saturated phenol:chloroform:isoamyl alcohol (25:24:1) in order to remove soluble proteins. DNA was precipitated from the solution by adding 0.1 volumes of 3 M sodium acetate, pH 5.2 and 2.5 volumes of cold 95% ethanol. After incubating for at least 1 hour at −20° C., the DNA was pelleted by centrifugation (5000×g for 20 min., 4° C.), rinsed with 10 mL 70% ethanol, air-dried and resuspended in 1 mL of 10 mM Tris, 1 mM EDTA, pH 8.0. RNA was digested by the addition of Ribonuclease A (Roche Diagnostics) added to a final concentration of 0.1 mg/mL and incubation at 37° C. for one hour. Sequential extractions with one volume of buffer-saturated phenol and one volume of buffer-saturated phenol: chloroform:isoamyl alcohol (25:24:1) were used to remove the ribonuclease from the DNA solution. The DNA was again precipitated with 0.1 volumes of 3 M sodium acetate, pH 5.2 and 2.5 volumes of cold 95% ethanol, pelleted by centrifugation, rinsed with 70% ethanol, air-dried and resuspended in 50 μL of 10 mM Tris, 1 mM EDTA, pH 8.0. The concentration of DNA was determined by measuring the absorbance of the solution at 260 nm (p. C1 in Sambrook et al., 1989, which is incorporated herein by reference).

The *T. reesei* cel5a gene, trcel5a, was amplified and modified to remove its intron by two-step PCR using trcel5a specific primers and the purified genomic DNA as a template. In the first PCR round, the first exon (coding DNA fragment) of trcel5a was amplified with primers 5'-EG2Nhe (SEQ ID NO:20) and 3'EG2-Delint (SEQ ID NO:21), whereas the second part was amplified with primers 5'EG2-Delint (SEQ ID NO:22) and 3'-EG2 Kpn (SEQ ID NO:23). These two amplicons were generated independently and shared a homologous sequence introduced with primers 3'EG2-Delint (SEQ ID NO:21) and 5'EG2-Delint (SEQ ID NO:22). In a second round of PCR, both products were ligated together and amplified with primers 5'-EG2Nhe and 3'-EG2 Kpn in order to generate the complete trcel5a gene without the intron. The final amplicon also contains the NheI and KpnI restriction sites upstream and downstream of the gene to allow cloning into the yeast vector. Introduction of the NheI site had the effect of changing the first two amino acids of the mature protein resulting in mutations Q1A and Q2S.

Primers used for removal of the intron from the trcel5a gene:

```
5'-EG2Nhe
                                        (SEQ ID NO: 20)
5' GAG CTA GCA CTG TCT GGG GCC AGT GTG G

3'EG2-Delint
                                        (SEQ ID NO: 21)
5' GGT AAC GCA AGT GCC ATC TGT GGT ACA

GCC AAA G

5'EG2-Delint
                                        (SEQ ID NO: 22)
5' TGG CAC TTG CGT TAC C 3'-EG2Kpn
                                        (SEQ ID NO: 23)
5' GAG GTA CCC TAC TTT CTT GCG AGA CAC GAG
```

Figure 2A:
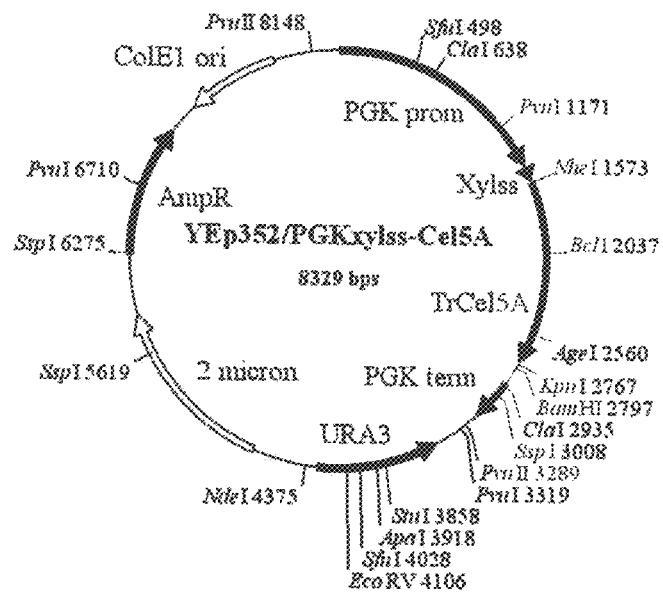
FIG. 2A is a vector map of YEp352/PGKxylss-Cel5A used to express native TrCel5A from *Saccharomyces cerevisiae* and to perform site-saturation mutagenesis.

The *Saccharomyces cerevisiae/Escherichia coli* vector, YEp352/PGK91-1ΔNheI-xylss-cbh2, was digested with NheI and KpnI to release its trcel6a insert. The fragments were separated on an agarose gel and a ~7.1 kb linearized vector fragment was purified from the gel using QIAquick Gel Extraction Kit (Qiagen). The final trcel5a PCR amplicon was digested with NheI and KpnI, ligated into the empty vector fragment and then transformed into *E. coli* strain DH5α chemically competent cells. The resulting vector was called YEp352/PGKxylss-Cel5A (FIG. 2A) and was transformed into the yeast strain YNL219C BY4742 [11993] using the procedure described by Gietz, R. D. and Woods, R. A. (2002).

Example 3

Making TrCel5A-G363X Site-Saturation Mutagenesis Library

A site-saturation library of the glycine at position 363 (G363X) of the mature native TrCel5A protein was made by two-step PCR using the YEp352/PGKxylss-Cel5A vector (FIG. 2A) as a template. In a first PCR round, the N-terminal region was amplified with primers XylSS (SEQ ID NO:24) and 3'E2-G363X (SEQ ID NO:25), whereas the C-terminal region was amplified with primers 5'E2-G363X (SEQ ID NO:26) and 3'PGK-term (SEQ ID NO:27). These two amplicons were generated independently and shared a homologous sequence introduced with primers 3'E2-G363X (SEQ ID NO:25) and 5'E2-G363X (SEQ ID NO:26). In a second round of PCR, both products were ligated together and amplified with primers XylSS (SEQ ID NO:24) and 3'PGK-term (SEQ ID NO:27) in order to generate the complete trcel5a gene saturated at amino acid position 363.

Primers used for site-saturation mutagenesis:

```
XylSS
                                        (SEQ ID NO: 24)
5' GAT CGT CGA CAT GGT CTC CTT CAC CTC CCT C
```

-continued

3'E2-G363X (SEQ ID NO: 25)
5' AAA TGA TCC GGC VNN CCA ACC AAC ATA

5'E2-G363X (SEQ ID NO: 26)
5' TAT GTT GGT TGG NNB GCC GGA TCA TTT

3'PGK-term (SEQ ID NO: 27)
5' GCA ACA CCT GGC AAT TCC TTA CC
V stands for A, C or G whereas B stands
for T, C or G.

To generate the TrCel5A-G363X library in the yeast expression vector, the YEp352/PGK91-1ΔNheI-xylss-cbh2 vector was digested with NheI and KpnI and the empty vector fragment was purified as described above. This linear fragment and the final trcel5a amplicon library were transformed simultaneously and cloned by in vivo recombination (Butler and Alcalde, 2003) into the yeast strain YNL219C BY4742 [11993].

Example 4

Isolation and Expression of TrCel5A-G363X from Microplate Cultures

This example describes the selection and expression of TrCel5A-G363X from *Saccharomyces cerevisiae* for use in a high-throughput screening assay (Example 5).

*Saccharomyces cerevisiae* transformants from Example 3 were grown on plates containing synthetic complete medium (SC: 2% agar w/v, 0.17% yeast nitrogen base w/v, 0.078%-Ura drop-out supplement w/v, 2% glucose w/v, 2% casamino acids w/v, 0.5% ammonium sulfate w/v, pH 5.5) containing 0.16% Azo-CMC (Megazyme) for 3 days at 30° C.

Colonies showing visible clearing halos were selected for liquid media cultures by toothpick inoculation of 150 µL synthetic complete (SC) media (SC: 0.17% yeast nitrogen base w/v, 0.078%-Ura drop-out supplement w/v, 2% glucose w/v, 2% casamino acids w/v, 0.5% ammonium sulfate w/v, pH 5.5) in 96-well microplates containing one glass bead (1.5-2.0 mm) per well. Pre-cultures were grown overnight (16-18 hours) at 30° C. and 300 rpm to stationary phase. The glycerol stocks were prepared by the addition of glycerol to a final concentration of 15% and stored at −80° C.

The glycerol stocks were used to start liquid media pre-cultures by using 10 µL of the glycerol stock to inoculate 150 µL synthetic complete media (SC: 0.17% yeast nitrogen base w/v, 0.078%-Ura drop-out supplement w/v, 2% glucose w/v, 2% casamino acids w/v, 0.5% ammonium sulfate w/v, pH 5.5) in 96-well microplates containing one glass bead (1.5-2.0 mm) per well. Pre-cultures were grown overnight (18-20 hours) at 30° C. and 300 rpm to stationary phase. For expression of the culture inoculation, 20 µL of pre-culture was used to inoculate 0.2 mL of SC media in microtitre plates containing one glass bead (1.5-2.0 mm). Expression cultures were grown for 3 days at 30° C. and 250 rpm with humidity control. Plates were centrifuged at 1,600×g for 5 minutes to pellet the cells and the supernatant was aspirated for screening assays.

Example 5

Screening of *Trichoderma reesei* Cel5A-G363X Library for Modified Family 5 Cellulases with Increased Specific Activity This example describes the screening of modified *Trichoderma reesei* TrCel5A cellulases for improved specific activity relative to the parental TrCel5A that had been cloned into *Saccharomyces cerevisiae*.

Modified TrCel5A cellulases from yeast microcultures, as described in Example 4, were tested in six 80 µL, Azo-CMC (Azo-carboxymethyl cellulose) activity assays, each at a different pH. An aliquot of supernatant from each microculture was added to 0.5% Azo-CMC (Megazyme) buffered with 50 mM citrate phosphate at pH 4.0, 5.0, 6.0, 6.5, 7.0 and 8.0 and incubated at 50° C. for 10 minutes. To stop the reaction, 200 µL, of precipitant solution (0.3 M sodium acetate trihydrate, 0.02 M zinc acetate dehydrate, 80% v/v anyhydrous ethanol) was added and the plates were centrifuged at 2,844×g for 10 minutes. A 0.1 mL aliquot of the supernatant was transferred to a microplate and the absorbance at 595 nm was measured. Contained in each 96-well plate were six parental TrCel5A controls used for comparison.

The concentration of TrCel5A cellulase in the *S. cerevisiae* microcultures was determined by ELISA. Microculture supernatants were diluted 160-fold while the purified component standard was diluted to 0.01-10 µg/mL (based on total protein) in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for 1 hour at room temperature. Blocked microtitre wells were washed with PBS/Tween. Rabbit polyclonal antisera specific for TrCel5A was diluted (1:4000) in PBS/BSA, added to the blocked microtitre plates and incubated for 2 hours at room temperature. Plates were washed and incubated with a goat anti-rabbit antibody coupled to horseradish peroxidase (Sigma #A6154), diluted 1:2000 in PBS/BSA, for 1 hour at room temperature. After washing, tetramethylbenzidine was added to each plate and incubated for 30 minutes at room temperature. The absorbance at 360 nm was measured in each well and converted into protein concentration using the TrCel5A standard curve.

The specific activity of the modified and the parental TrCel5A cellulases at each of the six pH values was calculated by dividing the absorbance value by the amount of the modified or parental TrCel5A cellulase, as determined by ELISA, present in the assay. The specific activities for the parental TrCel5A cellulase controls were fit with the following model to determine the $pK_{a2}$ value:

$$A = A_{max}\left(\frac{10^{-pH}}{10^{-pK_{a2}} + 10^{-pH}}\right)\left(\frac{10^{-pK_{a1}}}{10^{-pK_{a1}} + 10^{-pH}}\right) \quad \text{Eqn. 1}$$

A, which is a measured parameter, represents enzyme activity at the specific set experimental pH. $A_{max}$, $pK_{a1}$ and $pK_{a2}$ are all parameters that are determined by fitting the model to the data. $A_{max}$ represents the maximum activity of the enzyme, which will occur at its pH optimum. $pK_{a1}$ and $pK_{a2}$ represent the pH-dependence of the protonation of catalytically active residues.

A 95% confidence interval for the $pK_{a2}$ was determined and from that, the standard deviation on the $pK_{a2}$ was calculated. The same model was fit to the specific activities of each modified TrCel5A to calculate a $pK_{a2}$. The $pK_{a2}$ of each modified TrCel5A was compared to the $pK_{a2}$ of the parental TrCel5A controls and positives were selected at the 95% level of confidence using a t-test. To determine improvements in specific activity, the model was used to calculate the specific activity of the parental and modified TrCel5A cellulase at a pH corresponding to each enzyme's $pK_{a2}$. Positives were selected at the 95% confidence using a t-test. All positive modified TrCel5A endoglucanases were produced again in microculture and re-screened to reduce the number of false positives.

Figure 2B:
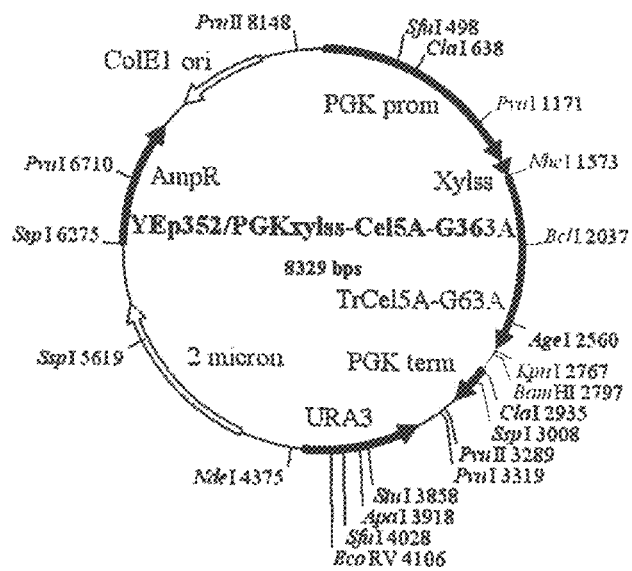
FIG. 2B is a vector map of YEp352/PGKxylss-Cel5A-G363A used to express TrCel5A-G363A from *Saccharomyces cerevisiae*.

From that screening, plasmids from positive clones were isolated from the yeast cultures using the method modified from Hoffman and Winston (1987) transformed into *E. coli* strain DH5α, and subsequently sequenced. After sequencing, the TrCel5A-G363A, TrCel5A-G363S and TrCel5AG363T modified cellulases were identified and the vectors that carried these modified Family 5 cellulases were named YEp352/PGKxylss-Cel5A-G363A (FIG. 2B), YEp352/PGKxylss-Cel5A-G363S and YEp352/PGKxylss-Cel5A-G363T, respectively.

Example 6

Expression of TrCel5A-G363A in *Trichoderma reesei*

Example 6.1

Host *Trichoderma* Strain for the Overexpression of TrCel5A-G363A

The host *Trichoderma reesei* strains used for the overexpression of modified TrCel5A-G363A were BTR213aux and P285-6aux.

Figure 3A:
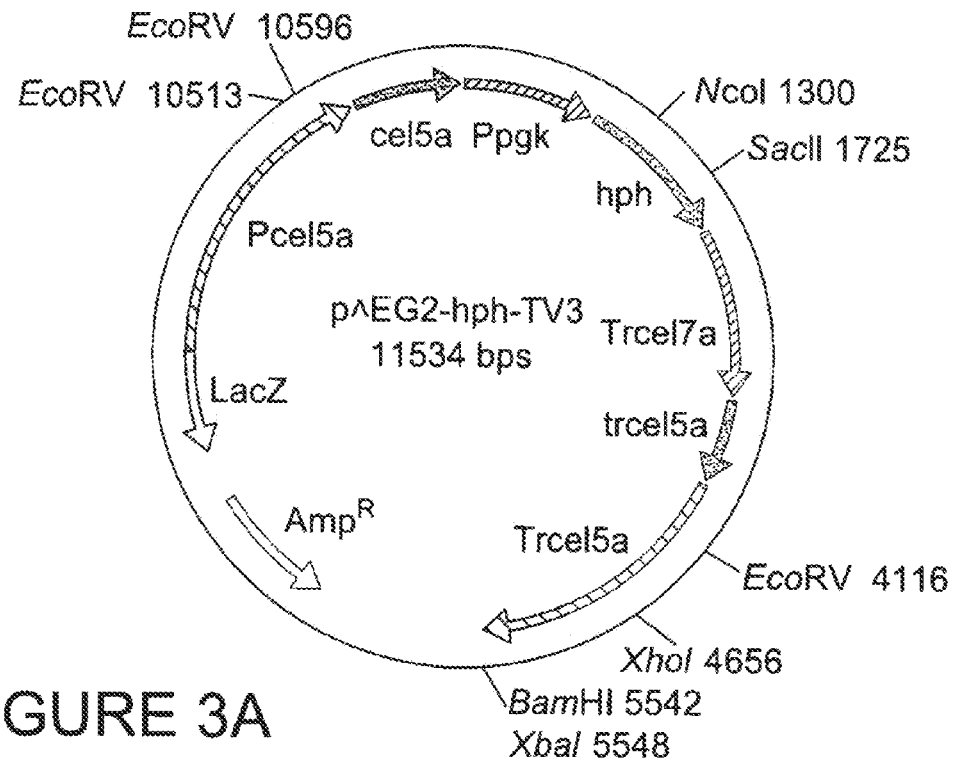
FIG. 3A is a vector map of the transformation vector p^EG2-hph-TV3 used to delete the endogenous cel5a gene from *Trichoderma reesei* to create strain P285-6.

The BTR213aux was isolated as described in Example 1. The P285-6aux strain was generated by transformation of BTR213aux with the p^EG2-hph-TV3 vector (FIG. 3A) which resulted in the deletion of the endogenous cel5a gene as described in co-pending and co-owned WO 2010/060188.

Example 6.2

Construction of the *Trichoderma reesei* Transformation Vector

Figure 3B:
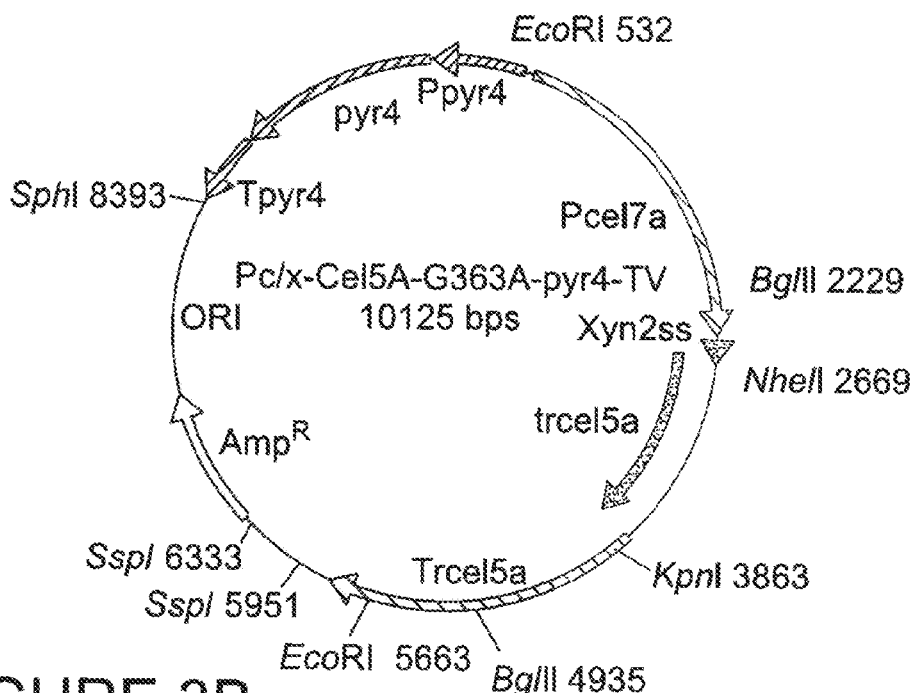
FIG. 3B is a vector map of transformation vector Pc/x-Cel5A-G363A-pyr4-TV.

The integrative *T. reesei* transformation vector, Pc/x-Cel5A-G363A-pyr4-TV (FIG. 3B), was constructed as follows. The yeast expression vector YEp352/PGKxylss-cel5A-G363A possessing the modified trcel5a (described in Example 5) was digested with NheI and KpnI restriction enzymes. The DNA fragments were separated on agarose gels and the fragment corresponding to the mature TrCel5A-G363A coding region was gel extracted using Wizard® SV Gel and PCR clean-up System (Promega). The isolated fragment was ligated via NheI and KpnI restriction enzyme digestion and ligation to produce the *Trichoderma* transformation vector Pc/x-Cel5A-G363A-pyr4-TV, which operatively links the mature TrCel5A-G363A coding region with a fragment comprising the xyn2 secretion signal coding sequence linked to a chimeric cel7A/xyn2 promoter (described in U.S. Pat. No. 6,015,703) and cel6a terminator. The generated *Trichoderma* transformation vector, Pc/x-cel5A-G363A-pyr4-TV, contains the *N. crassa* pyr4 gene as a selectable marker. This construct was transformed into chemically-competent DH5α *E. coli* cells. The TrCel5A-G363A coding region in the generated transformation vector was sequenced to verify the presence of the G363A mutation. To generate sufficient DNA for transformation into *Trichoderma*, *E. coli* cells containing transformed plasmid were grown overnight in 50 mL of liquid LB media supplemented with 100 μg/mL ampicilin with shaking at 37° C. Plasmid for the *Trichoderma* transformation was isolated using Wizard® Plus Midiprep kit (Promega) as described in the manufacture's protocol.

Since the trcel5a gene without the intron was used in the TrCel5A-G363A expression cassette, the trcel5a-G363A gene in the final Pc/x-cel5A-G363A-pyr4-TV transformation vector is shorter than the native genomic *T. reesei* cel5a gene by 179 nucleotides, the size of the intron.

Example 6.3

Transformation in *Trichoderma reesei*

TrCel5A-G363A overexpressing strains were generated by linearizing vector Pc/x-cel5A-G363A-pyr4-TV with SspI and transforming the vector into *Trichoderma* strains BTR213aux and P285-6aux by polyethylene glycol mediated transformation of protoplasts. Transformants were selected on minimal media plates lacking uridine to select for complementation of pyr4 auxotrophy in BTR213aux and P285-6aux.

The *Trichoderma* transformation was performed by the following procedure. $5 \times 10^6$ spores of the BTR213 and P285-6 auxotrophs were plated onto sterile cellophane on Potato Dextrose agar supplemented with 5 mM uridine and were incubated for 20 hours at 30° C. to facilitate spore germination and mycelial growth. Cellophane discs with mycelia were then transferred to 10 mL of a protoplasting solution containing 7.5 g/L driselase and 4 g/L beta-glucanase (InterSpex Products Inc., Cat. Nos. 0465-1 and 0439-2, respectively) in 50 mM potassium phosphate buffer, pH 6.5 containing 0.6 M ammonium sulfate (Buffer P). The fungal mycelia were digested for 5 hours with gentle agitation at 60 rpm. Protoplasts were separated from undigested mycelia by filtration through sterile No. 30 MIRACLOTH™ and collected into a sterile 50 mL round-bottom centrifuge tube and recovered by centrifugation at 1000-1500×g for 10 minutes at room temperature. Protoplasts were washed with 5 mL of Buffer P and centrifuged again at 1000-1500×g for 10 minutes at room temperature. Protoplasts were resuspended in 1 mL of STC buffer (1.2 M sorbitol, 10 mM $CaCl_2$, 10 mM Tris-HCL, pH 7.5). For transformation, 0.1 mL of resuspended protoplasts was combined with 10 μg of vector DNA and 0.025 mL of PEG solution (25% PEG 3350, 50 mM $CaCl_2$, 10 mM Tris-HCl, pH 7.5). After incubation in an ice water bath for 30 minutes, 1 mL of PEG solution was added and the mixture incubated for 5 minutes at room temperature. The transformation mix was diluted with 2 mL of STC buffer and the entire mix was added to 50 mL of molten MMSS agar media (Table 2 below) cooled to about 47° C., split in half, and poured over MMSS agar. Plates were incubated at 30° C. until colony growth was visible. Transformants were transferred to individual plates containing MM agar (Table 2) and allowed to sporulate. Spores were collected and plated at high dilution on MM agar to isolate homokaryon transformants, which were then plated onto PDA to allow for growth and sporulation.

TABLE 2

| Minimal medium (MM) agar | |
|---|---|
| Component* | Amount per L |
| $KH_2PO_4$ | 10 g |
| $(NH_4)_2SO_4$ | 6 g |
| $Na_3Citrate \cdot 2H_2O$ | 3 g |
| $FeSO_4 \cdot 7H_2O$ | 5 mg |
| $MnSO_4 \cdot H_2O$ | 1.6 mg |
| $ZnSO_4 \cdot 7H_2O$ | 1.4 mg |
| $CaCl_2 \cdot 2H_2O$ | 2 mg |
| Agar | 20 g |

TABLE 2-continued

| Minimal medium (MM) agar | |
|---|---|
| Component* | Amount per L |
| 20% Glucose f.s. | 50 mL |
| 1M MgSO$_4$•7H$_2$O f.s. | 4 mL |
| | pH to 5.5 |

*MMSS agar contains the same components as MM agar plus 1.2M sorbitol, 6.6 g/L YNB (Yeast Nitrogen Base w/o Amino Acids from DIFCO Cat. No. 291940) and 1.92 g/L amino acids (-Ura DO Supplement from Sigma Cat. No. Y1501-20G).

Example 6.4

Characterization of *Trichoderma reesei* Transformants

Figure 4:
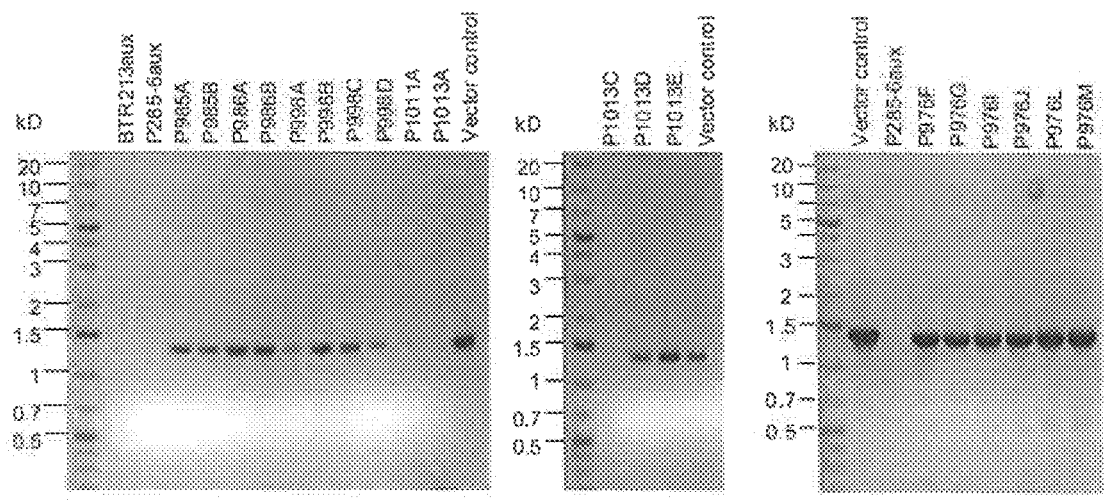
FIG. 4 is an agarose gel showing PCR amplification of the integrated TrCel5A-G363A expression cassette from genomic DNA of genetically modified *Trichoderma reesei* strains. DNA from the parental strains, BTR213aux and P285-6aux, and the TrCel5A-G363A expression vector were used as controls. The source of the template DNA is indicated at the top of each lane and the size of each DNA marker is indicated on the left of each panel.

Chromosomal integration of the transformation vector in isolated *T. reesei* transformants was confirmed by PCR using the Extract-N-Amp™ Seed PCR Kit (Sigma) and primers XylSS (5' GAT CGT CGA CAT GGT CTC CTT CAC CTC CCT C-3'; SEQ ID NO:24) and KW127 (5'-GGA ACC ACA CCA TCG CAC ATC-3'; SEQ ID NO:28). Template DNA preparation and PCR reactions were performed according to the manufacturer's recommendations. A fragment comprising the trcel3a-G363A coding region was amplified from the DNA isolated from all transformants but not DNA isolated from their parental strains (FIG. 4).

To test the production of the modified TrCel5A-G363A cellulase, spores of *Trichoderma* transformants and the parental strain grown on PDA plates were suspended in sterile water and about $10^4$-$10^6$ spores per mL were used to inoculate each micro-culture in 24-deepwell plates. The components present in the micro-culture media are provided in Table 3 below.

TABLE 3

| The composition of micro-culture media | |
|---|---|
| Component* | g/L |
| KH$_2$PO$_4$ | 8 |
| (NH$_4$)$_2$SO$_4$ | 12.7 |
| MgSO$_4$•7H$_2$O | 4 |
| CaCl$_2$•2H$_2$O | 1.02 |
| Corn steep liquor | 5 |
| CaCO$_3$ | 20 |
| Carbon source** | 35 |
| Trace elements* | 2 mL/L |

*Trace elements solution contains 5 g/L FeSO$_4$•7H$_2$O; 1.6 g/L MnSO$_4$•H$_2$O; 1.4 g/L ZnSO$_4$•7H$_2$O.
**Glucose, Solka floc, lactose, cellobiose, sophorose, corn syrup, or Avicel. The carbon source can be sterilized separately as an aqueous solution at pH 2 to 7 and added to the remaining media initially or through the course of the fermentation.

Figure 5:
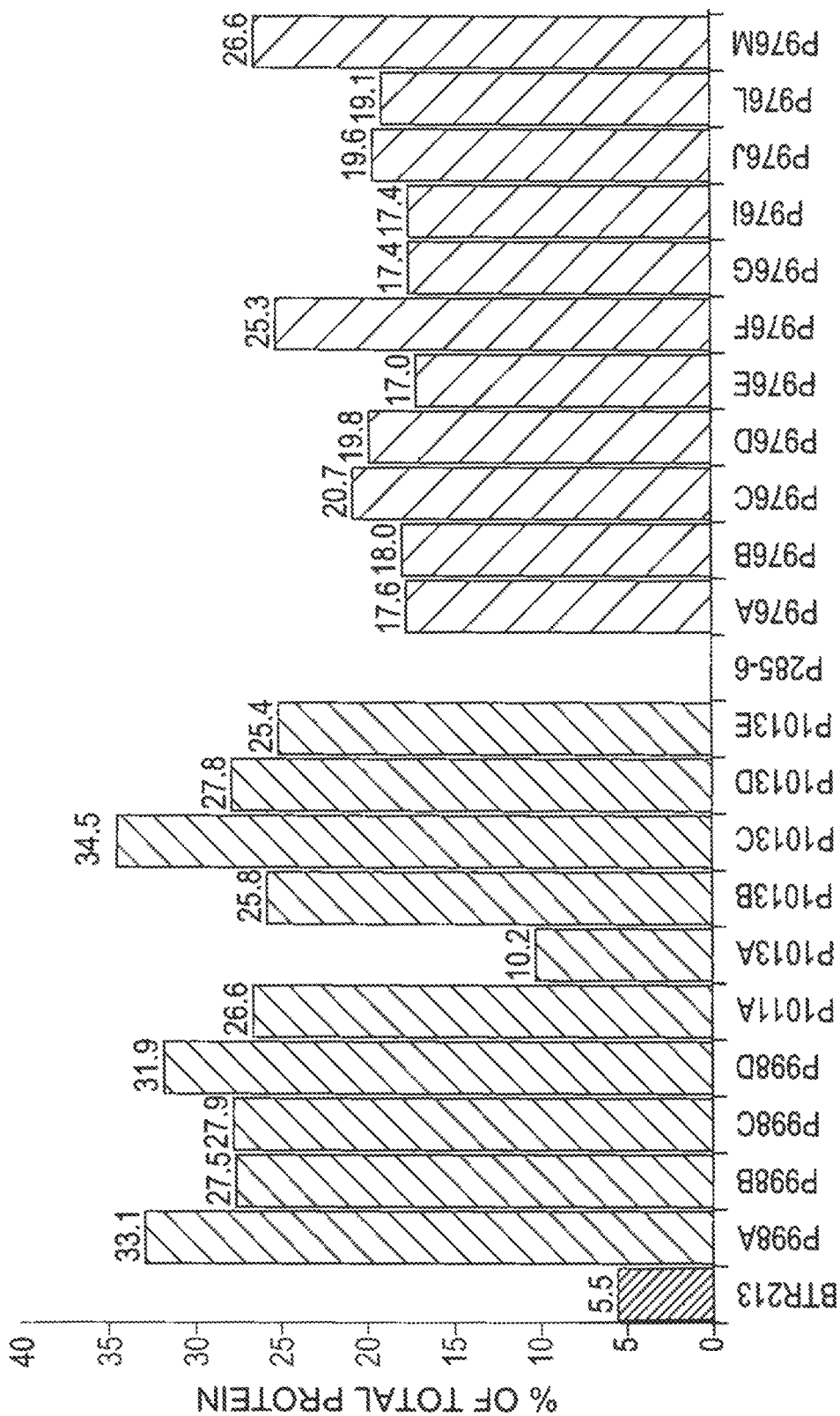
FIG. 5 shows the concentration of TrCel5A, expressed as the mass percent of the component as a fraction of total secreted protein, from BTR213, P285-6 and their transformant *Trichoderma reesei* strains overexpressing TrCel5A-G363A grown in 14 L fermentations. The strain names are shown under each bar.
Figure 6:
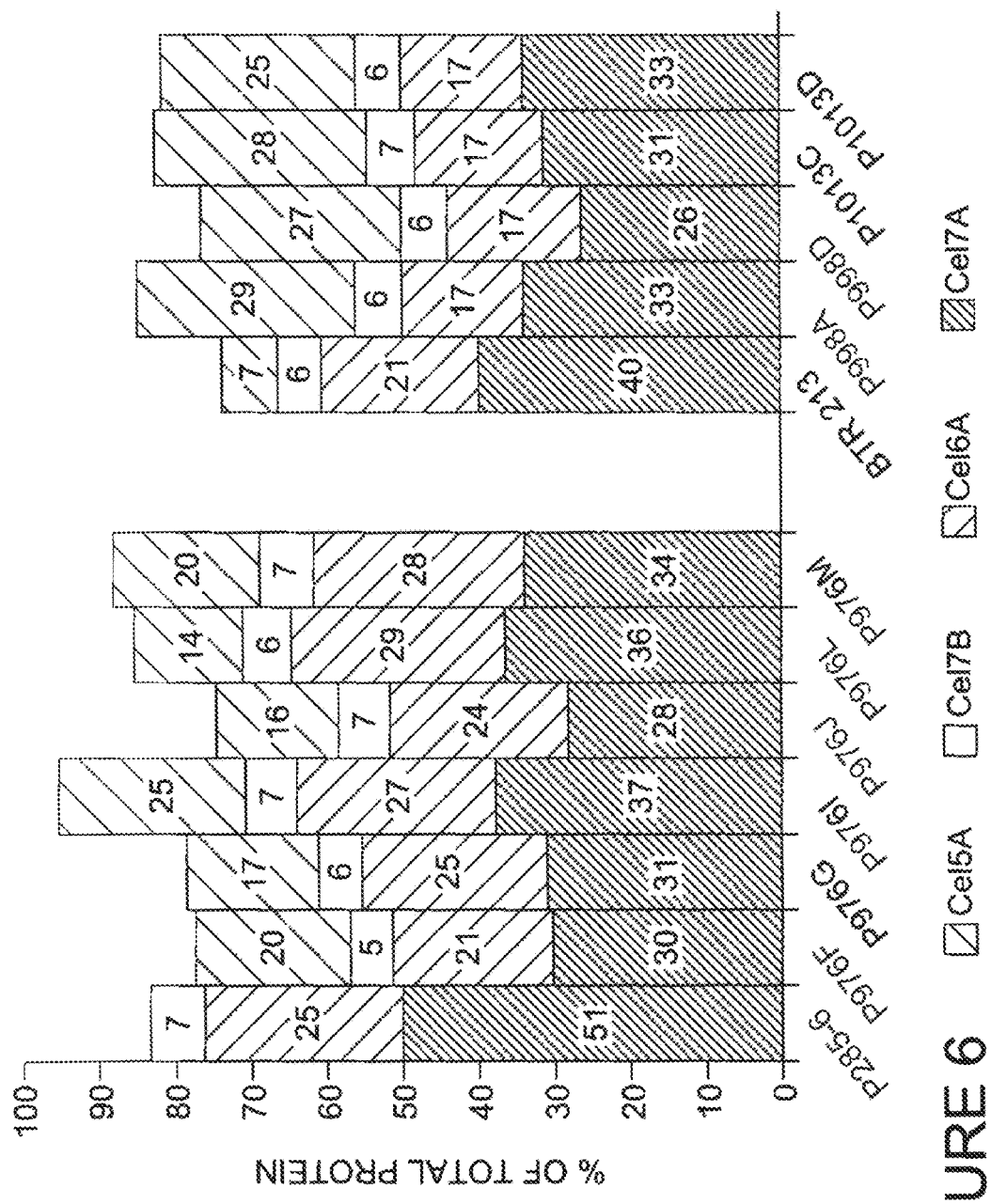
FIG. 6 shows the composition of the major *Trichoderma* cellulase components, Cel5A, Cel7B, Cel6A and Cel7A, in cellulase mixtures produced by BTR213, P285-6 and their transformant strains overexpressing TrCel5A-G363A grown in 14 L fermentations. The strain names are shown under each bar.
Figure 7:
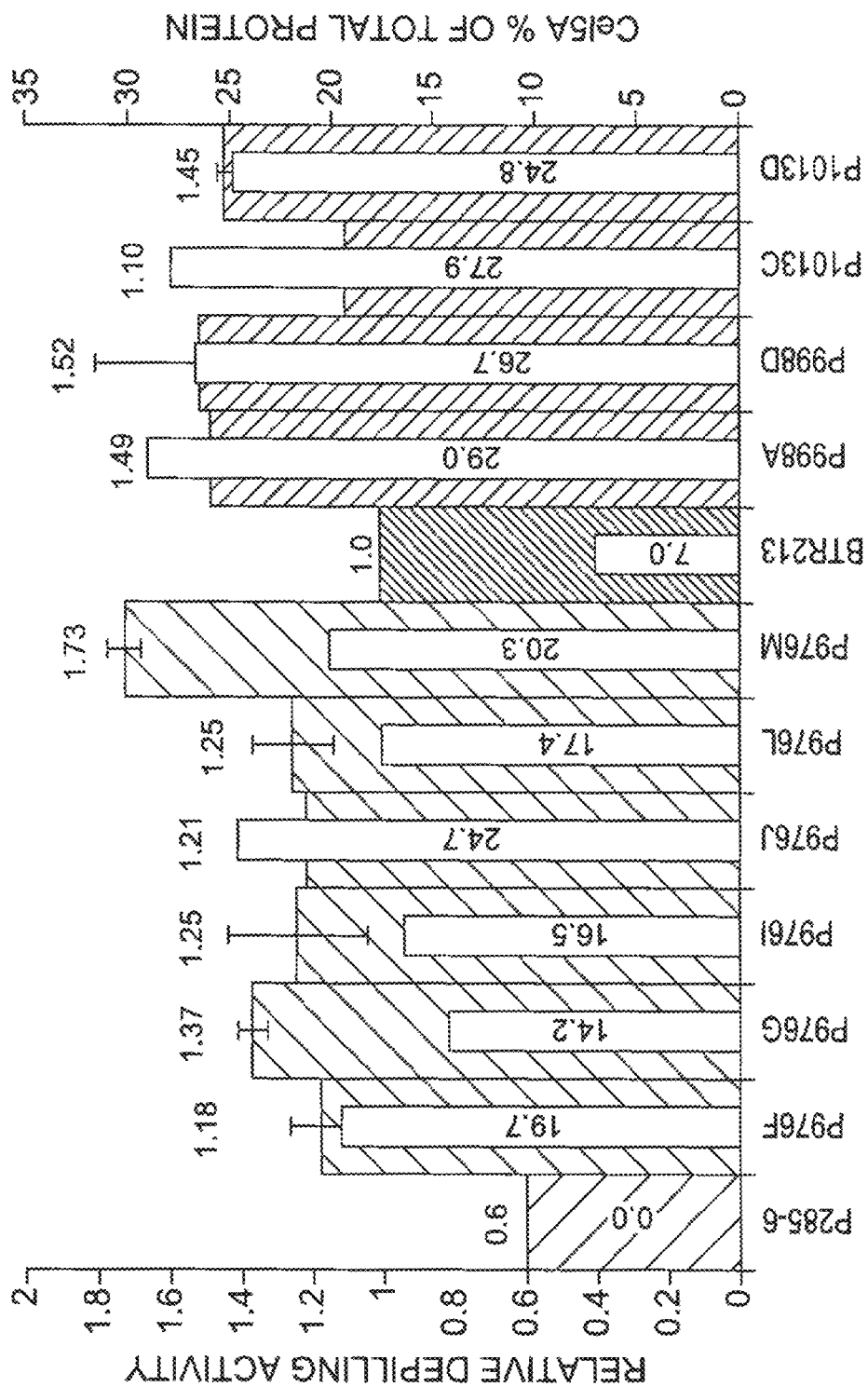
FIG. 7 shows the abundance of parental and modified TrCel5A (G363A) cellulases and the relative depilling activity of cellulase enzyme mixtures produced by strains expressing parental or modified TrCel5A cellulases. White bars indicate the abundance of modified TrCel5A plus parental (as % of total protein) produced by different *T. reesei* strains grown in 14 L fermentation (values are indicated on the middle of each bar). The amount of TrCel5A in each strain is indicated. Cross-hatched bars indicate the relative depilling activity of cellulase enzyme mixtures. Activity is expressed as the specific activity per unit of protein and normalized to depilling activity of a control cellulase enzyme mixture comprising only parental TrCel5A and values are indicated on the top of each bar. The strain names are shown under each bar.

Cultures were grown for 6 days at 30° C. with shaking at 250 rpm. The fungal cells were separated from the growth media containing the secreted protein by centrifugation at 12,000 rpm. The protein concentration was determined using the Bio-Rad Protein Assay (Cat. No. 500-0001). The relative abundance (in weight % of total secreted protein) of TrCel5A cellulases (modified and parental) was determined by ELISA. Culture supernatants and purified component standards were diluted to 0.01-10 μg/mL in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for one hour at room temperature. Blocked microtitre wells were washed with PBS/Tween. Rabbit polyclonal antiserum specific for TrCel5A was diluted in PBS/BSA, added to separate microtitre plates and incubated for 2 hours at room temperature. Plates were washed and incubated with a goat anti-rabbit antibody coupled to horseradish peroxidase (Sigma #A6154), diluted 1:2000 in PBS/BSA, for one hour at room temperature. After washing, tetramethylbenzidine was added to each plate and incubated for 30 minutes at room temperature. The absorbance at 360 nm was measured in each well and converted into a protein concentration using a TrCel5A standard curve. The concentration of total TrCel5A cellulase (modified and parental) was expressed as the mass percent of the component as a fraction of total secreted protein (FIG. 5). Several strains producing the highest amounts of TrCel5A cellulase (modified and parental) were selected for further analysis in 14 L fermentations (FIG. 6) and depilling assays (FIG. 7).

Example 7

Enzyme Production in 14 L Fermentations

*Trichoderma* spores of strains BTR213, P285-6 and selected transformants grown on PDA media were suspended in sterile water and transferred to 2 L, baffled Erlenmeyer flasks containing 750 mL of liquid Berkley media (pH 5.5) supplemented with 5.1 g/L of corn steep liquor powder and 10 g/L glucose (Table 4). Flasks were incubated at 28° C. for 3 days using an orbital agitator (Model G-52 New Brunswick Scientific Co.) running at 100 rpm.

TABLE 4

| Berkley media for flasks | |
|---|---|
| Component | g/L |
| (NH$_4$)$_2$SO$_4$ | 10.4 |
| KH$_2$PO4 | 2.0 |
| MgSO$_4$•7H$_2$O | 0.31 |
| CaCl$_2$•2H$_2$O | 0.53 |
| Dry Corn Steep Liquor | 5.1 |
| Glucose | 10 |
| Trace elements* | 1 mL/L |

*Trace elements solution contains 5 g/L FeSO$_4$•7H$_2$O; 1.6 g/L MnSO$_4$•H$_2$O; and 1.4 g/L ZnSO$_4$•7H$_2$O.

The contents of an inoculum flask were transferred to a 14 L pilot scale fermentation vessel (Model MF114 New Brunswick Scientific Co.) set up with 10 L of Initial Pilot Media (pH 5.5). The vessel was run in batch mode until glucose in the media was depleted. At this point, the carbon source containing cellulase inducing carbohydrates was added on a continuous basis from a stock that was 35.5% w/v of solids dissolved in water. Peristaltic pumps were used to deliver the carbon source at a feed rate of 0.4 grams of carbon per liter culture per hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.5 during cellulase production using an automated controller connected to an online pH probe and a pump enabling the addition of a 10% ammonium hydroxide solution. Periodically, 100 mL samples of broth were drawn for biomass and protein analysis.

TABLE 5

Initial media for fed-batch fermentations

| Component | g/L |
|---|---|
| $(NH_4)_2SO_4$ | 2.20 |
| $KH_2PO_4$ | 1.39 |
| $MgSO_4 \cdot 7H_2O$ | 0.70 |
| $CaCl_2 \cdot 2H_2O$ | 0.185 |
| Dry Corn Steep Liquor | 6.00 |
| Glucose | 13.00 |
| Trace elements* | 0.38 mL/L |

*Trace elements solution contains 5 g/L $FeSO_4 \cdot 7H_2O$; 1.6 g/L $MnSO_4 \cdot H_2O$; and 1.4 g/L $ZnSO_4 \cdot 7H_2O$.

The concentration of fungal cells in the culture broth was determined using aliquots of 5-10 mL that had been weighed, vacuum filtered through glass microfiber filters, and oven dried at 100° C. for 4 to 24 hours. The concentration of fungal cells was determined according to Equation 2 below.

$$\text{Biomass}\left(\frac{g}{L}\right) = \frac{\text{dry filter paper and cake }(g) - \text{filter mass}}{\text{wet sample mass }(g)} \times \text{broth density}\left(\frac{g}{mL}\right) \times 1000\frac{mL}{L}$$

The protein concentration of the culture filtrate was determined using the BioRad protein assay. Colour intensity changes in the Coomassie Brilliant Blue G-250 dye, that forms the basis of this assay, were quantified spectrophotometrically using absorbance measurements at 595 nm. The standard assay control used was a cellulase mixture of known composition and concentration. The final filtrates for enzyme analysis were collected after 162-170 hours.

The relative concentrations (in weight percent of total secreted protein) of four cellulase components (TrCel7A, TrCel6A, TrCel7B, total modified TrCel5A and parental TrCel5A) were determined by ELISA using a component specific antibody as described above (Example 6.4). The abundance of the three major cellulase components, Cel7A, Cel6A and Cel7B, is similar in the cellulase mixtures produced by transformants and parental strains. The abundance of TrCel5A cellulases (modified and parental) in the P998A, P998D, P1013C and P1013D cellulase mixtures increased by about four-fold compared to that of the parental BTR213 cellulase mixture due to the overexpression of the modified TrCel5A-G363A cellulase (FIG. 6). The P285-6 transformants P976F, P976G, P976I, P976J, P976L and P976M produced cellulase mixtures comprising 14-25% modified TrCel5A-G363A cellulases (FIG. 6).

Example 8

Depilling Activity of Enzyme Produced by *T. reesei* Transformants

To test depilling activity, circles of flannelette with an approximate diameter of 11.5 cm were cut out of a larger piece of fabric and weighed. The fabric was then placed in plastic jars with screw-top lids, and held against the bottom of the jar with gaskets made of rubber tubing. Subsequently, 90 g of 0.5 cm diameter steel ball bearings were added to each jar. The enzymes were diluted to deliver 10-100 units of CMC activity (as determined by Ghose et al., 1987) and 1-10 mg of the total protein per jar. The diluted enzyme was added to the jars so that the total liquid in each jar was about 15 g.

The jars were then sealed with their lids and incubated at 50° C. with 180 rpm orbital shaking for 2 hours in a shaker incubator. After incubation, 3 drops of 10 N NaOH were added to each jar to stop the enzymatic reaction. The liquid portion of each reaction was then passed through a pre-weighed glass fiber filter using a vacuum manifold and side-arm flasks. An additional 200 mL of water were added to each jar, still containing the immobilized flannelette disc, which was then closed and shaken by hand to release any fines trapped within the fabric. The filter papers were dried in a 100° C. oven for a minimum of 4 hours. The weights of the filter papers and captured fines were measured and used to calculate the percent weight loss of the substrate relative to the starting mass of each fabric disc.

The loss of fabric weight was calculated using Equation 3 below:

$$\% \text{ weight loss} = \frac{(\text{weight of the filter paper} + \text{collected fines}) - (\text{weight of filter paper})}{\text{initial weight of the fabric}} \times 100$$

The depilling was expressed as specific depilling activity per unit of protein and normalized to depilling activity of enzyme produced by strain BTR213.

As shown in FIG. 7, the overexpression of modified TrCel5A-G363A cellulase increased depilling activity of enzymes produced by either BTR213aux or P285-6aux transformants. These findings demonstrate that improved activity upon introduction of TrCel5A-G363A is observed whether the wild-type TrCel5A cellulase is present, as in the BTR213 transformants, or absent, as in the P285-6 transformants.

Example 9

Expression and Preparation of Parental and Modified TrCel5A Cellulases for Subsequent Activity Assays TrCel5A, TrCel5A-G363A, TrCel5A-G363S and TrCel5A-G363T preparations were made from transformed *S. cerevisiae* strains as set forth below and their respective specific activities were subsequently determined in a reducing end assay and a viscosity assay (Examples 10 and 11).

250 mL volumes of sterile SC*-Ura media (0.77 g/L—Ura drop out supplement, 1.7 g/L yeast nitrogen base, 5 g/L $(NH_4)_2SO_4$, 20 g/L casamino acids, 20 g/L glucose) were inoculated with 10 mL of overnight cultures of transformed *Saccharomyces cerevisiae* grown from cells freshly picked from an agar plate. The cultures were then incubated for 72 hours at 30° C. with shaking at 250 rpm.

After incubation, the yeast cultures were centrifuged for 10 minutes at 3,300×g. The supernatant was removed with a pipette and retained and the yeast cell pellet was discarded. The concentration of parental or modified TrCel5A in the supernatant was determined using an ELISA with a standard curve of purified TrCel5A. This TrCel5A (parental or modified) preparation was used in viscosity assays (Example 11) without further treatment.

For the reducing ends assay (Example 10), the supernatant was concentrated and desalted to reduce the background signal of the assay. The yeast culture supernatants containing parental or modified TrCel5A cellulase were exchanged into a citrate-phosphate buffer (5 mM citrate, 5 mM phosphate, pH 6.0) using Centricon® plus-20 Biomax PES-5 (Amicon) filtration devices. The supernatants were successively concentrated by passage through a Centricon® device in 3 centrifugation steps of 10-15 minutes at 3,450×g to the minimum retention volume of the device. The flow-through was discarded after each step. The concentrated, retained enzyme solution was then re-suspended in buffer and centrifuged as described above. The flow-through was discarded and the protein accumulated on the membrane was re-suspended in 10 mL of buffer and transferred in a 50 mL Falcon™ tube. Buffer was added to 40 mL final volume. The concentration of buffer-exchanged parental or modified TrCel5A was determined using an ELISA with a standard curve of purified TrCel5A.

Example 10

Assay for Creation of Reducing Ends by TrCel5A, TrCel5A-G363A or TrCel5A-G363S Acid swollen cellulose (ASC) was produced from Sigma-Cell50 (Sigma-Aldrich) using procedures known to those skilled in the art. The ASC was slurried in water to a concentration of 3.5 g of cellulose/L and homogenized in five cycles of 1 minute "on" followed by 1 minute "off" using a rotor-stator homogenizer with a probe diameter of 1 cm. The cellulose slurry or "ASC slurry" was then degassed under vacuum for 10 minutes with constant stirring.

Endoglucanases create new reducing ends in cellulose, some of which are associated with the insoluble substrate and some of which are associated with short, solubilized cellodextrins. The number of reducing ends in the substrate prior to enzymatic treatment and the reducing potential of the enzyme itself, collectively termed a no-activity control, can be directly measured by mixing enzyme and substrate under conditions of high pH (10 or higher) where enzymatic hydrolysis of cellulose will not Occur.

Aliquots containing 125 µL of the ASC slurry were dispensed by pipetting into microplates with 96 wells of 2 mL volume each. The slurry was mixed on a stir plate during dispensing to ensure homogeneous substrate distribution. An equal volume of 100 mM Na Citrate/Phosphate buffer, of varying pH, was added to each well. The plate was sealed with aluminum sealing tape and preheated in a 50° C. water bath for 15 minutes. The plate was unsealed and 125 µL of buffer-exchanged TrCel5A, TrCel5A-G363A or TrCel5A-G363S was added to triplicate wells (0.4 µg of enzyme were added to each reaction). The plate was resealed and returned to the 50° C. waterbath to incubate for 30 minutes. To stop the reaction, the plate was unsealed and a volume of BCA working solution (0.971 g/L disodium 2,2'-bicinchoninate, 27.14 g/L $Na_2CO_3$, 12.1 g/L $NaHCO_3$, 0.624 g/L $CuSO_4.5H_2O$, 0.631 g/L L-Serine) equivalent to the sample volume was added to all samples.

Standard curves were generated simultaneously for each pH tested on each reaction microplate and used for the conversion of absorbance signal to reducing ends concentration, as glucose equivalents. Six glucose concentrations were used as standard solutions: 0.1 g/L, 0.05 g/L, 0.025 g/L, 0.0125 g/L, 0.006 g/L and 0 g/L. Aliquots of 125 µL of standard solutions were dispensed by pipetting in the microplate, along with equivalent volumes of pH buffer and TrCel5A.

The BCA reaction to measure reducing ends (based on Zhang and Lynd, 2005) was carried out at 75° C. for 30 minutes. The reaction was stopped by cooling the sealed plates under running room temperature water. The plate was centrifuged at 2,750×g for 4 minutes to sediment the remaining insoluble ASC. Next, 200 µL of supernatant from each well was transferred into a 96-well polystyrene microplate and the absorbance was read at 560 nm. Absorbance readings were converted into glucose equivalents using the standard curve and matching no-activity controls were subtracted from readings of wells with active enzyme and substrate. Corrected readings were converted into specific activities in units of micromoles of glucose produced per minute per milligram of enzyme.

The results of the empty vector controls were subtracted from those of the enzyme-containing samples for each pH point. For the control samples, an equivalent volume of empty vector supernatant (from the growth of S. cerevisiae containing an expression vector lacking a TrCel5A gene) was used instead of TrCel5A preparation. Equation 1 (see Example 5) was fit to the corrected data by minimization of the sum of the squared residuals and the best-fit values of $pK_{a1}$, $pK_{a2}$ and $A_{max}$ were determined.

Figure 8:
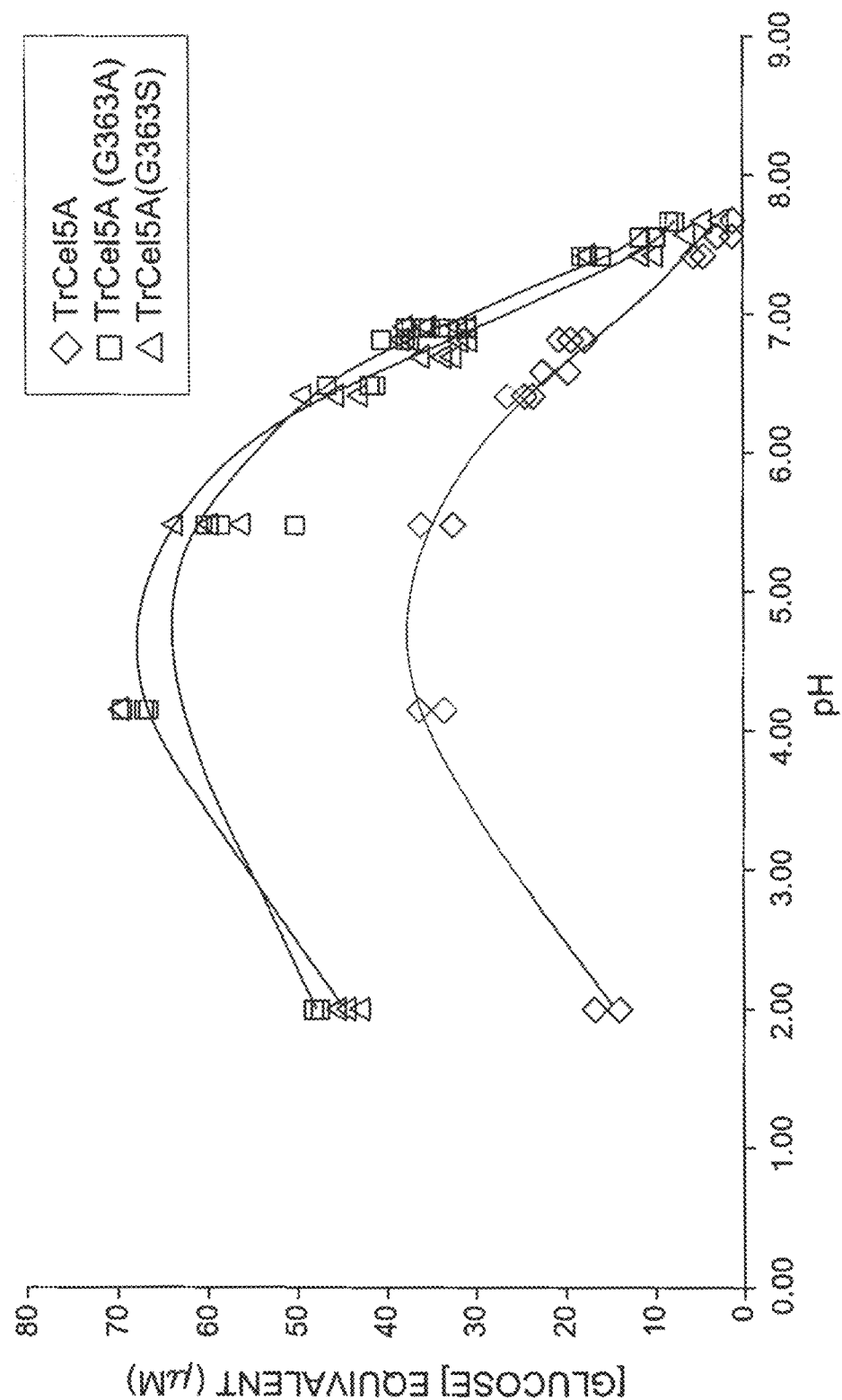
FIG. 8 shows TrCel5A, TrCel5A-G363A and TrCel5A-G363S activity on acid swollen cellulose (ASC) determined by measuring reducing sugar (depicted as glucose equivalents in μM) released over 30 minutes as a function of pH.

Activity of parental and modified TrCel5A cellulases as a function of pH, as well as model fits is depicted in FIG. 8. The upper and lower limits of the 95% confidence intervals for $pK_{a1}$, $pK_{a2}$ and $A_{max}$ were determined using the methods of Motulsky (2004). A t-test was performed to compare the $A_{max}$ of TrCel5A-G363A and TrCel5A-G363S to wild-type, parental TrCel5A and to calculate a P-value to determine whether the parameters of the modified Family 5 cellulase were significantly different from those for the wild-type cellulase (Table 6).

TABLE 6

Determination of P-values for $A_{max}$ of TrCel5A, TrCel5A-G363A and TrCel5A-G363S on acid swollen cellulose

| | $A_{max}$ | Standard Deviation | P-value |
|---|---|---|---|
| TrCel5A | 36.4 | 1.3 | |
| TrCel5A-G363A | 62.8 | 2.3 | 1.4E−13 |
| TrCel5A-G363S | 66.8 | 2.6 | 6.0E−14 |

These results show that the modified TrCel5A-G363A and TrCel5A-G363S cellulases are more active than the parental TrCel5A cellulase on acid swollen cellulose.

Example 11

Viscometric Assay of Activity of TrCel5A and TrCel5A-G363A

A hydroxyethyl cellulose (HEC) stock solution was prepared by first warming 1 L of water in a glass beaker to 40° C. on a heating plate. After warming, 50 g of HEC was slowly added and mixed with vigorous stirring using a stir bar. The beaker was covered with a plastic film to prevent evaporation and the cellulose was allowed to solubilize overnight at room temperature with mixing using a magnetic stir bar.

To assay TrCel5A activity (modified and parental), 15 g of HEC substrate was weighed into a disposable metal sample cup for the RVA-Super-4 viscometer (Newport Scientific). 5 mL of 400 mM Na Citrate/Phosphate buffer was added to the substrate and the vessel was pre-warmed in the instrument for two minutes at 50° C. Next, 2 mL of TrCel5A, TrCel5A-G363A or TrCel5A-G363T (not buffer-exchanged) was added to the pre-heated sample and allowed to react for 2.5 minutes, during which time the viscosity in centipoise was automatically recorded every second. For the control samples, an equivalent volume of empty vector supernatant (from the growth of S. cerevisiae containing an expression vector lacking a TrCel5A gene) was used instead of a preparation containing parental and/or modified TrCelA.

The slope of the plot of viscosity as a function of time was calculated after the mixing of the enzyme solution into the buffered substrate was complete (after approximately 20 seconds) and only for the apparently linear portion of the data.

Figure 9:
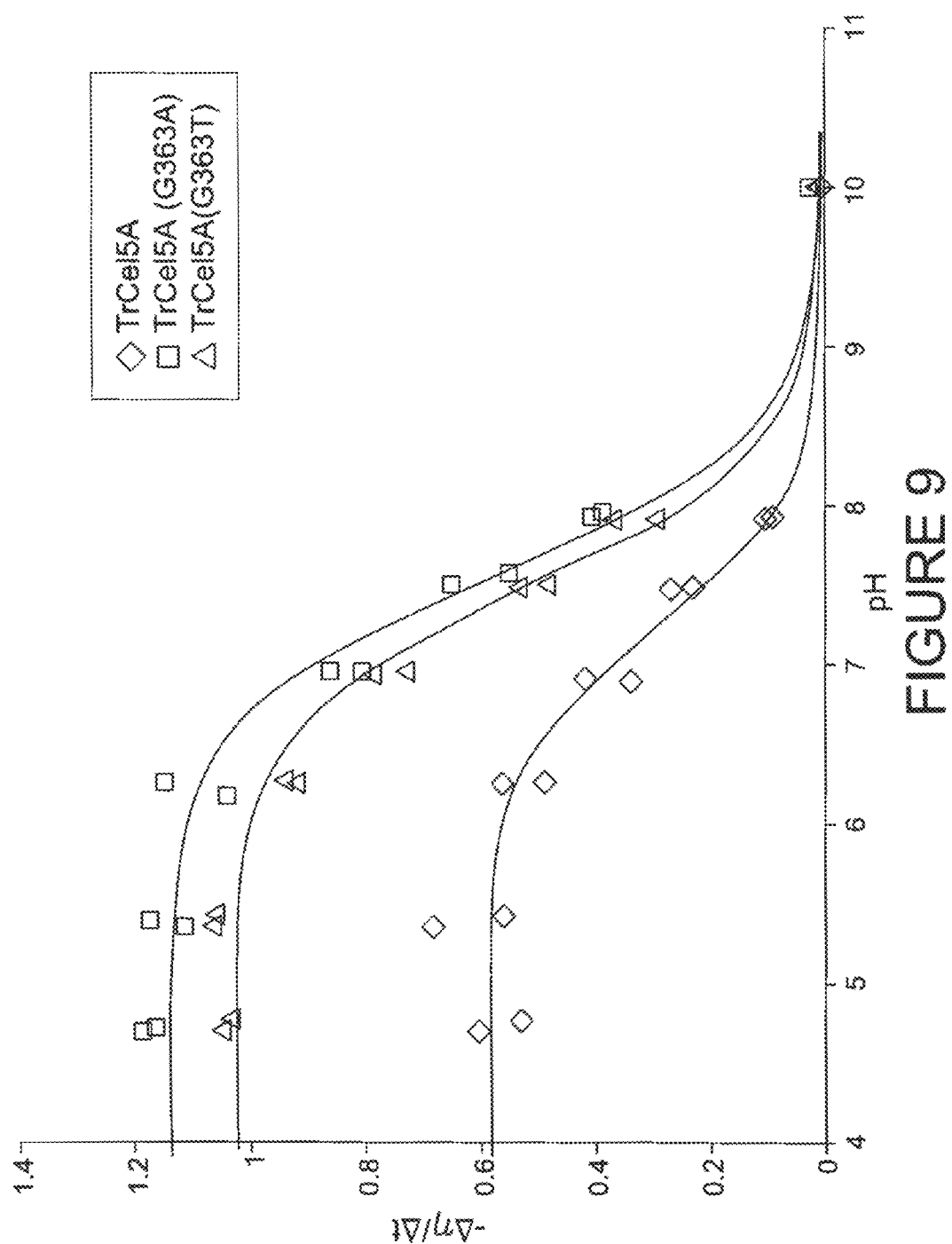
FIG. 9 shows TrCel5A, TrCel5A-G363A and TrCel5A-G363T activity on hydroxyethyl cellulose (HEC) determined by measuring the rate in change in viscosity with time ($-\Delta\eta/\Delta t$) as a function of pH.
Figure 10:
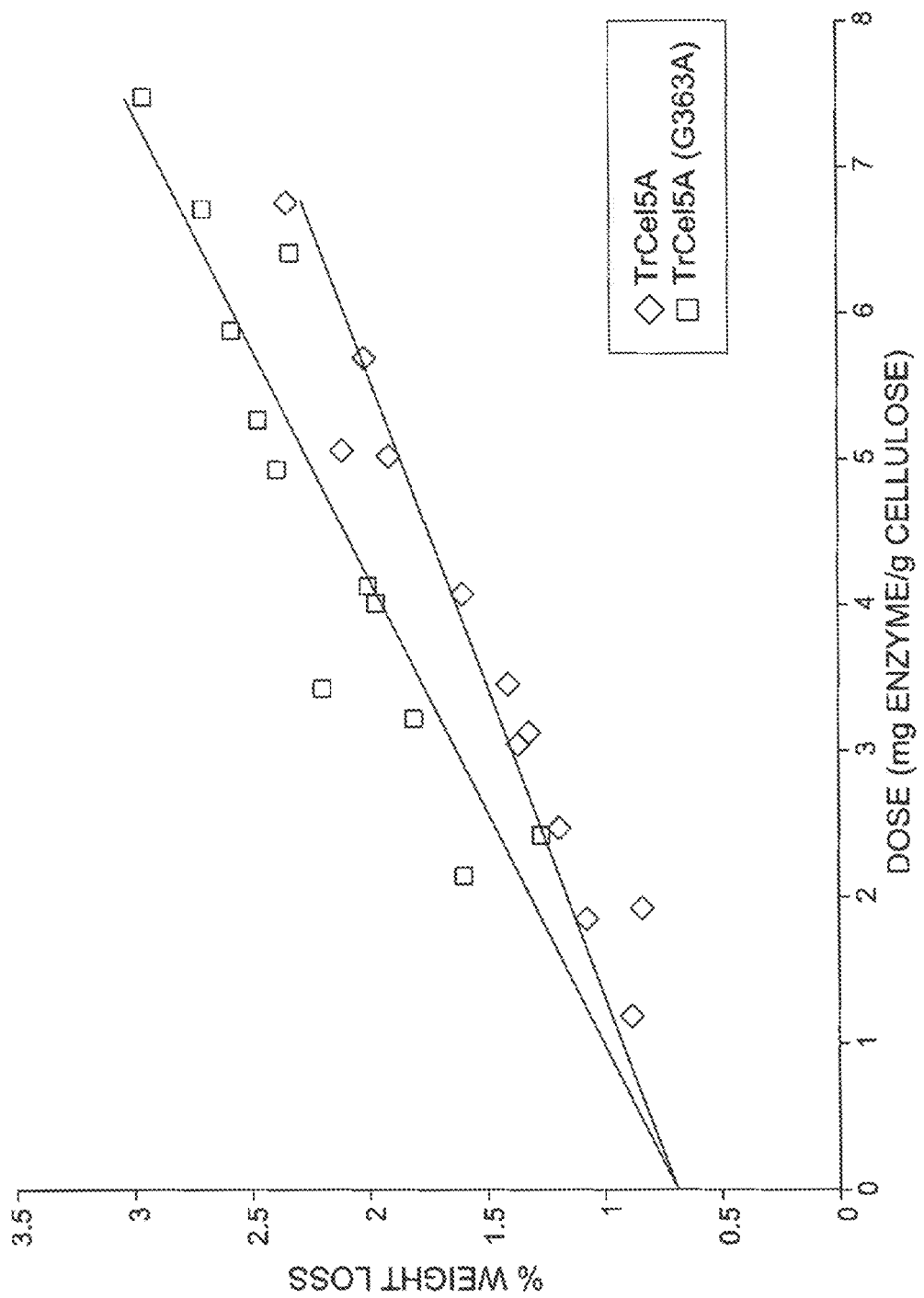
FIG. 10 shows the depilling efficacy of TrCel5A and TrCel5A-G363A as measured by percent weight loss of flannelette as a function of enzyme dose in mg of enzyme per g of substrate.

For each pH point, the slopes of the empty vector curves were subtracted from those of enzyme samples. Equation 1 set forth in Example 5 was fit to the corrected data by minimization of the sum of the squared residuals and the best-fit values of $pK_{a1}$, $pK_{a2}$ and $A_{max}$ were determined. Values of $pK_{a1}$ from the BCA assay (Example 10) were used for these fits. TrCel5A activity as a function of pH, and model fits, are depicted in FIG. 9. The upper and lower limits of the 95% confidence intervals for all three parameters were determined using the methods of Motulsky (2004). A t-test was performed to compare the $A_{max}$ of TrCel5A-G363A and TrCel5A-G363T to TrCel5A and to calculate a P-value to determine whether the parameters of the modified Family 5 cellulase were significantly different from those of the parental TrCel5A cellulase (Table 7).

TABLE 7

Determination of P-values for $A_{max}$ of TrCel5A, TrCel5A-G363A and TrCel5A-G363T on hydroxyethyl cellulose.

| | $A_{max}$ | Standard Deviation | P-value |
|---|---|---|---|
| TrCel5A | 0.59 | 0.04 | |
| TrCel5A-G363A | 1.14 | 0.04 | 4.9E−14 |
| TrCel5A-G363S | 1.03 | 0.03 | 2.1E−13 |

These results show that the modified TrCel5A-G363A and TrCel5A-G363S cellulases are more active than the parental TrCel5A cellulase on hydroxyethyl cellulose.

Example 12

Purification of TrCel5A and TrCel5A-G363A Expressed from *Trichoderma reesei*

A strain of *Trichoderma reesei* was grown in submerged liquid fermentation under conditions that induce cellulase production as described in Example 7. The crude mixture of *Trichoderma* proteins were secreted by the cells into the fermentation broth. The fungal cells were removed from the fermentation broth by filtration across a glass microfiber filter containing a Harborlite filter bed. TrCel5A or TrCel5A-G363A was separated from the crude filtrate by anion exchange chromatography using a DEAE-Sepharose column as described by Bhikhabhai et al. (1984). Purified TrCel5A or TrCel5A-G363A was concentrated and buffer exchanged into 50 mM sodium citrate, pH 5.0 using a stirred ultrafiltration cell (Amicon) and a 10 kDa nominal molecular weight cutoff polyethersulfone membrane.

Example 13

Assay of the Depilling Activity of TrCel5A and TrCel5A-G363A

The effectiveness of an enzyme in removing small balls of fuzz, referred to as pills, from fabric is measured by direct weighing of released insoluble cellulose from fabric.

Depilling assays were conducted as described in Example 8. Stocks of purified TrCel5A or TrCel5A-G363A in 50 mM citrate, pH 5.0, were added to 6 jars in 1 mL increments from 2 to 7 mL. Additional citrate buffer was added to a final volume of 50 mL.

The slope of the plot for TrCel5A is 0.233 percent wt loss/(mg enzyme/g cellulose) and 0.311 percent wt loss/(mg enzyme/g cellulose) for TrCel5A-G363A, indicating a 34% increase in activity of the modified Family 5 cellulase by this measure. An F-test was used to compare the global fit performed with two slopes and a single intercept with a model of one slope and one intercept, a null model in which TrCel5A and TrCel5A-G363A have equivalent activities (Motulsky, 2004). This null model is rejected (P=0.0002) by the F-test.

REFERENCES

Altschul, S. F., Gish, W., Miller, W., Myers, E. W. and Lipman, D. J. (1990) Basic local alignment search tool. J. Mol. Biol. 215:403-410.

Altschul, S. F., Madden T. L., Schäffer, A. A., Zhang, J., Zhang, Z., Miller, W., Lipman D. J. (1997) Gapped BLAST and PSI-BLAST: a new generation of protein database search programs. Nuc. Acids Res. 25:3389-3402.

Ausubel, F. M, Brent, R. Kingston, R. E., Moore, D. D., Seidman, J. G., Struhl, K. 1995 supplement Current Protocols in Molecular Biology, John Wiley & Sons, Ausubel et al., eds.

Baker, J. O., McCarley, J. R., Lovett, R., Yu, C. H., Adney, W. S., Rignall, T. R., Vinzant, T. B., Decker, S. R., Sakon, J., and Himmel, M. E. (2005) Catalytically enhanced endocellulase Cel5A from *Acidothermus cellulolyticus*. Appl. Biochem. Biotechnol. 121-124:129-148.

Bhikhabhai, R., Johansson, G. and Petterson, G. (1984) Isolation of Cellulolytic Enzymes from *Trichoderma reesei* QM 9414. Journal of Applied Biochemistry, 6:336-345.

Butler, T. and Alcalde, M. (2003) In Methods in Molecular Biology, vol. 231: (F. H. Arnold and G. Georgiou, editors), Humana Press Inc. Totowa (N.J.), ppg. 17-22).

Cantarel, B. L., Coutinho, P. M., Rancurel, C., Bernard, T., Lombard, V., and Henrissat, B. (2008) The Carbohydrate-Active EnZymes database (CAZy): an expert resource for Glycogenomics. Nucleic. Acids. Res. 37:D233-D238.

Davies, G. and Henrissat, B. (1995) Structures and mechanisms of glycosyl hydrolases. Structure. 3(9): 853-9.

Eijsink, V. G. H, Gåseidnes, S., Borchert, T. V., van den Burg, B. (2005) Directed evolution of enzyme stability. Biomolecular engineering. 22(1-3):21-30.

Fukuda, T., Ishikawa, T., Ogawa, M., Shiraga, S., Kato, M., Suye, S., and Ueda, M. (2006) Enhancement of cellulase activity by clones selected from the combinatorial library of the cellulose-binding domain by cell surface engineering. Biotechnol. Prog. 22:933-938.

Ghose, T. K. (1987) Measurement of cellulase activities. Pure & Appl. Chem. 59(2):257-268.

Gietz, R. D. and Woods, R. A. (2002) Transformation of yeast by the Liac/SS Carrier DNA/PEG Method. Methods in Enzymology 350:87-96.

Hoffman, C. S. and Winston, F. (1987) A ten-minute DNA preparation from yeast efficiently releases autonomous plasmids for transformation of *Escherichia coli*. Gene 57:267-272.

Ito, J., Fujita, Y., Ueda, M., Fukuda, H., and Kondo, A. (2004) Improvement of cellulose-degrading ability of a yeast strain displaying *Trichoderma reesei* endoglucanase II by recombination of cellulose-binding domains. Biotechnol. Prog. 20:688-691.

Lin, L., Meng, X., Liu, P., Hong, Y., Wu, G., Huang, X., Li, C., Dong, J., Xiao, L., Liu, Z. (2008) Improved catalytic efficiency of Endo-beta-1,4-glucanase from *Bacillus subtilis* BME-15 by directed evolution. Appl. Microbiol. Biotechnol. 82:671-679.

Ly, H. D. and Withers, S. G. (1999) Mutagenesis of glycosidases. Annu Rev. Biochem. 68:487-522.

Macarron, R., van Beeumen, J., Henrissat, B., de la Mata, I., and Claeyssens, M. (1993) Identification of an essential glutamate residue in the active site of endoglucanase III from *Trichoderma reesei*. FEBS Lett. 316:137-140.

Montencourt, B. S., Schamhart, D. H. J., Cuskey, S. M., Eveleigh, D. E. (1979) Improvements in cellulase production by *Trichoderma* through mutation and selected breeding. Proc. 3$^{rd}$ Annual Symp. On Fuels from Biomass, Golden Colo., pp. 85-89.

Motulsky, H. and Christopolous, A., 2004, "Fitting Models to Biological Data Using Linear and Nonlinear Regression: A Practical Guide to Curve Fitting", Oxford University Press (2004).

Nakamura, A., Fukumori, F., Horinouchi, S., Masaki, H., Kudo, T., Uozumi, T., Horikoshi, K., and Beppu, T. (1991) Construction and characterization of the chimeric enzymes between the *Bacillus subtilis* cellulase and an alkalophilic *Bacillus* cellulase. J. Biol. Chem. 266:1579-1583.

Needleman, S. B. and Wunsch, C. D. (1970) A general method applicable to the search for similarities in the amino acid sequence of two proteins. J. Mol. Biol. 48:443-453.

Park, J. S., Hitomi, J., Horinouchi, S., and Beppu, T. (1993) Identification of two amino acids contributing the high enzyme activity in the alkaline pH range of an alkaline endoglucanase from a *Bacillus* sp. Protein Eng. 6:921-926.

Pearson W. R. and Lipman D. (1988) J. Proc Natl Acad Sci. Improved tools for biological sequence comparison. 85(8): 2444-8.

Qin, Y., Wei, X., Song, X., and Qu, Y. (2008a) The role of the site 342 in catalytic efficiency and pH optima of endoglucanase II from *Trichoderma reesei* as probed by saturation mutagenesis. Biocatal. Biotransformation. 26:378-382.

Qin, Y., Wei, X., Song, X., and Qu, Y. (2008b) Engineering endoglucanase II from *Trichoderma reesei* to improve the catalytic efficiency at a higher pH optimum. J. Biotechnol. 135:190-195.

Sambrook, T., Fritsch, E. F. and Maniatis T. (1989) Molecular Cloning: A Laboratory Manual, Second Edition, Cold Spring Harbor Press.

Smith, T. F. and Waterman, M. S. (1981) Comparison of biosequences, Adv. Appl. Math., 2:482-489.

Stahlberg, J., Johansson, G., and Pettersson, G. (1988) A binding-site-deficient, catalytically active, core protein of endoglucanase III from the culture filtrate of *Trichoderma reesei*. Eur. J. Biochem. 173:179-183.

Wang, T., Liu, X., Yu, Q., Zhang, X., Qu, Y., Gao, P., and Wang, T. (2005) Directed evolution for engineering pH profile of endoglucanase III from *Trichoderma reesei*. Biomol. Eng. 22:89-94.

Wang, Q., Tull, D., Meinke, A., Gilkes, N. R., Warren, A. J., Aebersold, R. and Withers, S. G. (1993) Glu280 is the nucleophile in the active site of *Clostridium thermocellum* CelC, a Family A endo-β-1,4-glucanase. The Journal of Biological Chemistry. 268(19):14096-14102.

Xiao, Z., Wang, P., Qu, Y., Gao, P., and Wang, T. (2002) Cold adaptation of a mesophilic cellulase, EG III from *Trichoderma reesei*, by directed evolution. Sci. China, C, Life Sci. 45:337-343.

Zhang, Y.-H. P. and Lynd, L. R. (2005) Determination of the number-average degree of polymerization of cellodextrins and cellulose with application to enzymatic hydrolysis. Biomacromolecules, 6:1510-1515.

The invention claimed is:

1. A modified Family 5 cellulase comprising a substitution of an amino acid at position 363 with a non-native alanine, or serine or threonine, said position determined from alignment of the modified Family 5 cellulase amino acid sequence with amino acids 71 to 397 of SEQ ID NO:1, wherein the modified Family 5 cellulase contains no more than 20 other amino acid substitutions relative to a corresponding wild-type Family 5 cellulase, and wherein the modified Family 5 cellulase is derived from a fungal parental Family 5 cellulase which does not naturally possess an alanine, serine, or threonine at position 363.

2. The modified Family 5 cellulase of claim 1, wherein said modified Family 5 cellulase exhibits an increase in specific activity of at least about 1.2 fold relative to a parental Family 5 cellulase or a corresponding wild-type Family 5 cellulase.

3. The modified Family 5 cellulase of claim 1, wherein said fungal parental Family 5 cellulase is a Family 5 cellulase from a species of *Trichoderma, Hypocrea, Penicillium, Botryotinia, Macrophomina, Aspergillus, Orpinomyces, Pestalotiopsis, Myceliopthora,* or *Chrysosporium*.

4. The modified Family 5 cellulase of claim 1, wherein the substituted amino acid at position 363 is an alanine.

5. An enzyme mixture comprising the modified Family 5 cellulase of claim 1.

6. A process for bio-stoning, which process comprises a step of contacting denim fabric or denim garments with a modified Family 5 cellulase, or an enzyme mixture thereof, said modified Family 5 cellulase comprising a substitution of an amino acid at position 363 with a non-native alanine, serine or threonine, said position determined from alignment of the modified Family 5 cellulase amino acid sequence with amino acids 71 to 397 of SEQ ID NO:1, wherein the modified Family 5 cellulase is derived from a fungal parental Family 5 cellulase which does not naturally possess an alanine, serine, or threonine at position 363.

7. A process for depilling, which process comprises a step of contacting cellulose-containing goods with a modified Family 5 cellulase, or an enzyme mixture thereof, said modified Family 5 cellulase comprising a substitution of an amino acid at position 363 with a non-native alanine, serine or threonine, said position determined from alignment of the modified Family 5 cellulase amino acid sequence with amino acids 71 to 397 of SEQ ID NO:1, wherein the modified Family 5 cellulase is derived from a fungal parental Family 5 cellulase which does not naturally possess an alanine, serine, or threonine at position 363.

8. The process of claim 7, wherein in the step of contacting, the cellulose-containing goods are fabrics or garments.

9. A detergent composition comprising a modified Family 5 cellulase, or an enzyme mixture thereof, said modified Family 5 cellulase comprising a substitution of an amino acid at position 363 with a non-native alanine, serine or threonine, said position determined from alignment of the modified Family 5 cellulase amino acid sequence with amino acids 71 to 397 of SEQ ID NO:1, wherein the modified Family 5 cellulase is derived from a fungal parental Family 5 cellulase which does not naturally possess an alanine, serine, or threonine at position 363.

10. A genetic construct comprising a nucleic acid sequence encoding the modified Family 5 cellulase of claim 1.

11. A genetically modified microbe comprising the genetic construct of claim 10.

12. A process for producing the modified Family 5 cellulase of claim 1 or the enzyme mixture of claim 5, comprising the steps of growing the genetically modified microbe of claim 11 in a culture medium under conditions that induce the expression and secretion of the modified Family 5 cellulase and recovering an enzyme mixture comprising the modified Family 5 cellulase from the culture medium.

13. An enzyme mixture comprising one or more cellulases and a modified *Trichoderma reesei* Cel5A enzyme, said modified *Trichoderma reesei* Cel5A enzyme comprising a *Trichoderma reesei* Family 5 catalytic domain corresponding to amino acids 71-397 of SEQ ID NO: 1 and containing a substitution of a glycine at position 363 with alanine, and no more than 20 other amino acid substitutions in its sequence relative to amino acids 71 to 397 of SEQ ID NO: 1.

14. An enzyme mixture comprising one or more cellulases and a modified *Trichoderma reesei* Cel5A enzyme as set forth in SEQ ID NO: 17, SEQ ID NO: 18 or SEQ ID NO: 19.

15. The enzyme mixture of claim 14, which comprises the modified *Trichoderma reesei* Cel5A enzyme as set forth in SEQ ID NO: 17.

* * * * *